(12) United States Patent
Sharma et al.

(10) Patent No.: US 10,953,200 B2
(45) Date of Patent: Mar. 23, 2021

(54) DEVICE FOR COLLECTING MATERIAL FROM A BODY CAVITY

(71) Applicant: Department of Biotechnology, New Delhi (IN)

(72) Inventors: Amit K. Sharma, New Delhi (IN); Nishith Chasmawala, Gujarat (IN); Sandeep Singh, New Delhi (IN)

(73) Assignee: Department of Biotechnology, New Delhi (IN)

( * ) Notice: Subject to any disclaimer, the term of this patent is extended or adjusted under 35 U.S.C. 154(b) by 904 days.

(21) Appl. No.: 14/465,401

(22) Filed: Aug. 21, 2014

(65) Prior Publication Data
US 2015/0011955 A1    Jan. 8, 2015

Related U.S. Application Data

(63) Continuation of application No. 13/378,696, filed as application No. PCT/IN2010/000409 on Jun. 16, 2010, now Pat. No. 8,840,594.

(30) Foreign Application Priority Data

Jun. 18, 2009 (IN) .............................. 1252DEL2009
Dec. 4, 2009 (IN) .............................. 2502DEL2009

(51) Int. Cl.
*A61F 5/451* (2006.01)
*A61M 25/04* (2006.01)
*A61M 1/00* (2006.01)

(52) U.S. Cl.
CPC ............. *A61M 25/04* (2013.01); *A61F 5/451* (2013.01); *A61M 1/008* (2013.01);
(Continued)

(58) Field of Classification Search
CPC ........ A61M 25/04; A61M 1/00; A61M 1/008; A61M 1/0019; A61M 2205/0216;
(Continued)

(56) References Cited

U.S. PATENT DOCUMENTS

| 4,030,500 A | 6/1977 | Ronnquist |
| 4,067,335 A | 1/1978 | Silvanov |

(Continued)

FOREIGN PATENT DOCUMENTS

| WO | WO93/21880 A1 | 11/1993 |
| WO | WO97/43987 A1 | 11/1997 |

(Continued)

*Primary Examiner* — Ariana Zimbouski
(74) *Attorney, Agent, or Firm* — Shay Glenn LLP

(57) ABSTRACT

A collector for fecal discharge is provided comprising a self-expanding resilient collection component, a housing sheath and a transit component. The collection component has an open proximal and distal end and a lumen connecting them. The component comprises interconnected resilient arms circumscribing its contour, wherein adjacent arms are resiliently biased away from each other for exerting outwardly radial pressure for expanding and anchoring the component to rectal walls upon deployment. The housing sheath comprises a flexible and resilient material overlaying at least one of inner or outer contour of collection component without interfering with or blocking its ends or lumen. The transit component provides a conduit for fecal discharge to migrate from collection component to a receptacle and comprises a flexible, tubular sheath having a first open end connected to a second end by a lumen, wherein the first end engages with the proximal end of the collection component.

22 Claims, 21 Drawing Sheets

(52) U.S. Cl.
CPC ..... *A61M 1/0019* (2013.01); *A61M 2202/068* (2013.01); *A61M 2205/0216* (2013.01)

(58) Field of Classification Search
CPC ..... A61M 2202/068; A61M 2210/1067; A61F 5/451; A61F 5/0076; A61F 2/04; A61F 2002/045
See application file for complete search history.

(56) References Cited

U.S. PATENT DOCUMENTS

| | | |
|---|---|---|
| 4,117,847 A | 10/1978 | Clayton |
| 4,182,332 A | 1/1980 | Delaney |
| 4,496,356 A | 1/1985 | Lognion |
| 4,686,985 A | 8/1987 | Lottick |
| 4,784,656 A | 11/1988 | Christian |
| 4,799,928 A | 1/1989 | Crowley |
| 5,036,867 A | 8/1991 | Biswas |
| 5,224,494 A | 7/1993 | Enhorning |
| 5,261,898 A | 11/1993 | Polin et al. |
| 5,520,669 A | 5/1996 | Mulholland |
| 5,593,417 A | 1/1997 | Rhodes |
| 5,741,239 A | 4/1998 | Mulholland |
| 5,876,445 A | 3/1999 | Andersen et al. |
| 5,941,860 A | 8/1999 | Wheeler |
| 6,013,023 A | 1/2000 | Klingenstein |
| 6,189,535 B1 | 2/2001 | Enhorning |
| 6,342,052 B1 | 1/2002 | Allende |
| 6,527,755 B1 | 3/2003 | Salama |
| 6,645,137 B2 | 11/2003 | Ulmsten et al. |
| 6,818,015 B2 | 11/2004 | Hankh et al. |
| 6,939,289 B2 | 9/2005 | Zunker et al. |
| 7,025,791 B2 | 4/2006 | Levine et al. |
| 7,122,058 B2 | 10/2006 | Levine et al. |
| 7,476,256 B2 | 1/2009 | Meade et al. |
| 8,840,594 B2 | 9/2014 | Sharma et al. |
| 2002/0138052 A1 | 9/2002 | Perlo et al. |
| 2003/0055484 A1 | 3/2003 | Lau et al. |
| 2004/0078012 A1 | 4/2004 | Uno |
| 2005/0113933 A1 | 5/2005 | Carter et al. |
| 2006/0025798 A1 | 2/2006 | Cook et al. |
| 2006/0235448 A1 | 10/2006 | Roslin et al. |
| 2007/0135781 A1 | 6/2007 | Hart |
| 2008/0009814 A1 | 1/2008 | Bartning et al. |
| 2008/0133025 A1 | 6/2008 | Daignault et al. |
| 2008/0195226 A1* | 8/2008 | Williams ............. A61F 2/04 623/23.67 |
| 2009/0203959 A1 | 8/2009 | Ziv et al. |
| 2009/0216206 A1* | 8/2009 | Nishtala ............ A61M 39/10 604/327 |
| 2010/0152529 A1 | 6/2010 | Shalon et al. |

FOREIGN PATENT DOCUMENTS

| | | |
|---|---|---|
| WO | WO98/33458 A2 | 8/1998 |
| WO | WO00/36996 A1 | 6/2000 |
| WO | WO2009/015152 A1 | 1/2009 |

\* cited by examiner

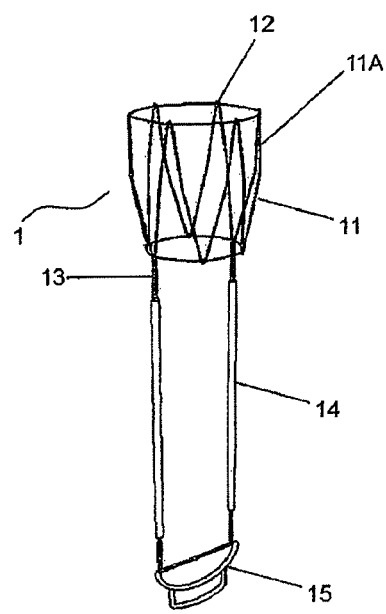
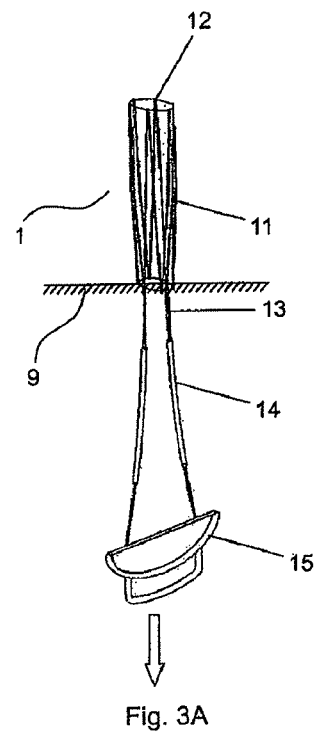
Fig. 3　　　　　　　　Fig. 3A
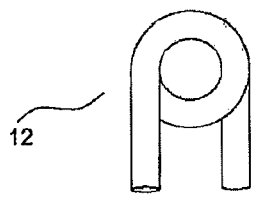
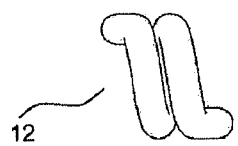
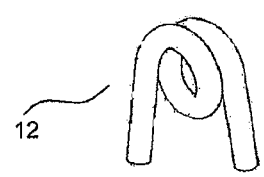
Fig. 4　　　　Fig. 4A　　　　Fig. 4B

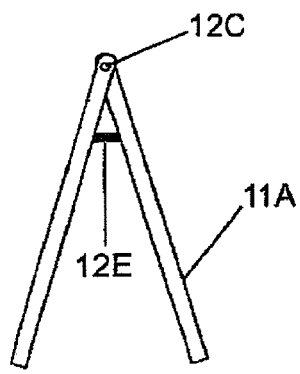
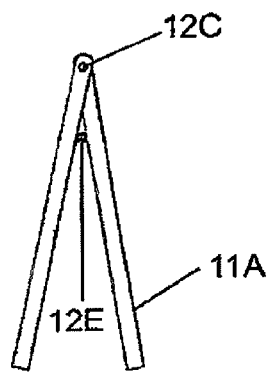
Fig. 4I    Fig. 4J
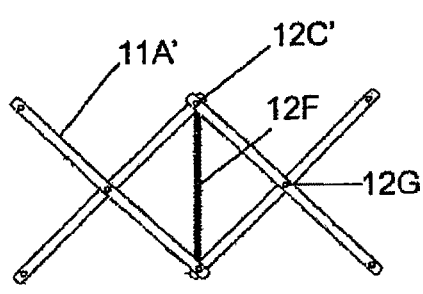
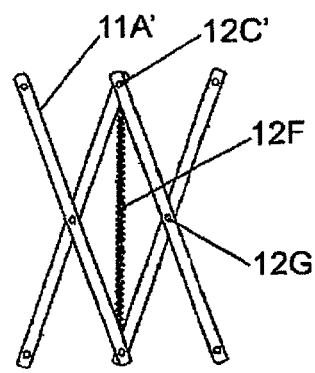
Fig. 4K    Fig. 4L

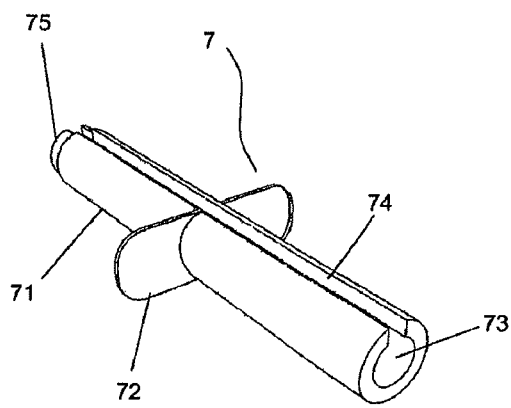
Fig. 12
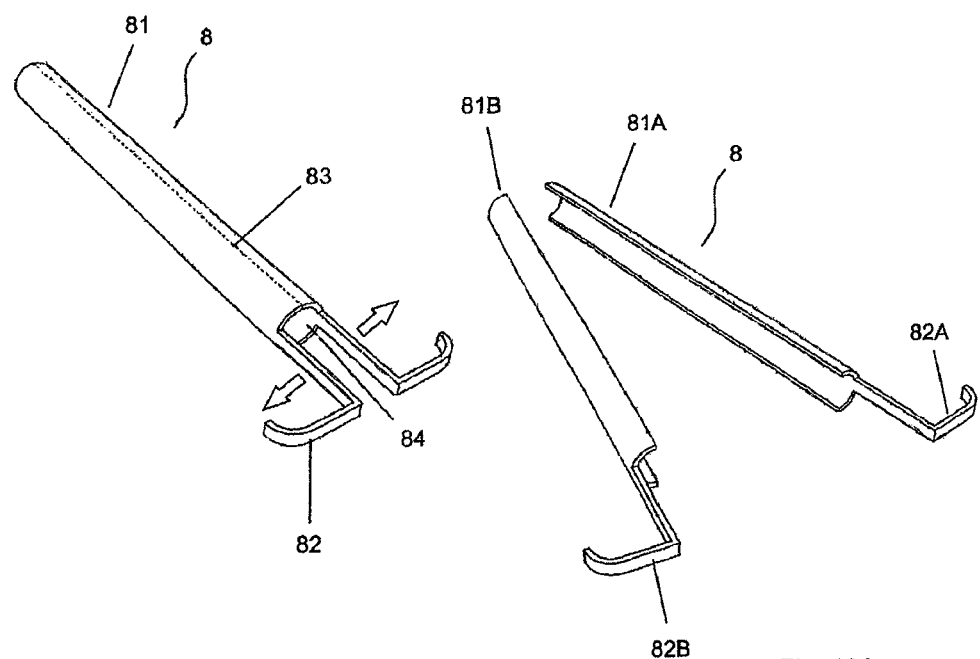
Fig. 13
Fig. 13A

DEVICE FOR COLLECTING MATERIAL FROM A BODY CAVITY

CROSS REFERENCE TO RELATED APPLICATIONS

This application is a continuation of U.S. patent application Ser. No. 13/378,696, filed Dec. 16, 2011, and titled "DEVICE FOR COLLECTING FECAL DISCHARGE IN INCONTINENT PATIENTS," Publication No. US 2012-0116336 A1, which is a 35 U.S.C. 371 National Phase Application of International Patent Application No. PCT/IN 10/00409, filed Jun. 16, 2010, titled "DEVICE FOR COLLECTING FECAL DISCHARGE IN INCONTINENT PATIENTS," published in English, Publication No. WO 2010/146602, which claims priority to India Application No. 2502/DEL/2009, filed Dec. 4, 2009 and India Application No. 1252/DEL/2009, filed Jun. 18, 2009, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention is related to a device for collecting fecal discharge, and devices and methods for deployment thereof.

BACKGROUND

The present invention relates to solutions for containment or management of fecal output. Options for containment or management of fecal output known in the art include absorbent pads in the form of diapers or sanitary napkins, anal plugs, fecal collectors in the form of collection bags or pouches, and indwelling catheters.

Of the various available solutions, indwelling catheters provide a promising solution for managing fecal incontinence. An indwelling catheter is placed inside the rectum and a retaining member comprising a resilient ring or an inflatable balloon or cuff is used to hold the catheter inside the rectum. The retaining member is delivered in a compressed state into the rectum through the anal opening, and is allowed to, or caused to expand within the rectum. In its expanded state, the retaining member abuts against the shelf provided by the anorectal junction (which provides a shelf at the junction between the broader passage of the rectum and the narrower anal canal) and is prevented from being unintentionally withdrawn from the rectum and through the anal opening. The retaining member also provides an annular lumen to allow passage of stool. The retaining member is connected to a collection bag, for feces.

Existing indwelling catheters have several shortcomings.

A primary drawback of prior art devices is that the retaining member is configured to assume and retain its expanded state within the rectum, causing the resilient ring or inflatable structure to apply a continuous externally directed radial force against the walls of the rectum, causing rectal tissue aggravation, mucosal damage, rectal stenosis, degeneration of the internal or external nerves and rupture of the superior rectal blood vessels.

Additionally, in the natural state, fecal matter is expelled from the colon and rectum by a wave like muscular contraction of the colon and rectal walls (peristalsis) and a corresponding relaxation of the sphincter. Peristaltic contractions cause the rectal walls to expand and contract to move fecal matter towards the anal opening. In cases where a prior art indwelling catheter has been inserted into the rectum, externally directed radial forces exerted by the retaining member interferes with peristaltic contractions at the point at which said member has been disposed within the rectum. The continual pressure exerted by the resilient member also causes damage to the rectal walls and to the internal or external sphincter leading to permanent dysfunction.

In certain cases, the resistance presented by the resilient member to the rectal walls during peristaltic contractions causes said resilient member itself to be expelled towards the anal opening, until it is forced to abut against the anorectal junction, or in some cases is expelled entirely from the anal canal.

Prior art devices additionally fail to taken into account physiology of the rectum and anal canal. The anorectal junction (the common boundary of the rectum and anal canal) provides a limiting boundary for particular nerve types. Visceral nerves are found above the anorectal junction, while somatic nerves are found below said junction. Somatic nerves are capable of sensing pain, while visceral nerves only sense pressure and not pain. By virtue of the somatic nerves, the anorectal junction and portions below it are extremely sensitive, and cause a high level of discomfort in case of foreign objects located within the anal canal.

A large number of prior art devices rely on a retaining member located at and abutting against the shelf provided by the anorectal junction. In other prior art devices, as a consequence of resistance of the retaining member to peristaltic contractions, said devices are moved as a consequence of the peristaltic contractions toward the anal opening, until they rest against the shelf provided by the anorectal junction. As a result of the retaining member residing at the anorectal junction, the patient is constantly aware of a foreign body sensation with resulting discomfort. For this reason, prior art devices have not been particularly successful for patients, other than those in intensive care.

In terms of effectiveness, prior art devices have so far only been successful with respect to non-solid fecal matter. Limitations to effectiveness have multiple causes. First, the anal canal and anorectal junction provide passages with a limited lumen diameter for passage of fecal matter. Situating a retaining member comprising either a continuous ring (or cylinder) of resilient material, or an inflated cuff or balloon, within the rectum further reduces the lumen diameter to a significant extent, which reduces the available volume for passage of fecal matter. The reduction in available lumen diameter precludes the passage of any significant quantity of solid fecal waste.

Another constraint faced by prior art devices is the likelihood of being dislodged. Regardless of whether the retaining member comprises a resilient ring or an inflatable cuff, the upper rim of such resilient ring or cuff (the rim which is furthest from the anal opening) presents an abutment surface against which descending fecal waste would necessarily impact. Pressure exerted by descending solid fecal waste against the abutment surface causes the retaining member to be dislodged, so that it no longer presents the complete annular lumen for passage of stool, consequently causing leakage or seepage along outside walls of the resilient member. Moreover, once dislodged, the resilient member presents an increased abutment surface area, against which pressure continues to be exerted by solid fecal waste, eventually leading to the entire device being expelled from the anal opening.

Owing to the limitations in addressing solid fecal discharge, usefulness of prior art devices is limited to addressing liquid fecal discharge, which is typically observed only in patients in intensive care.

Prior art devices also face a serious drawback in terms of leakage/seepage caused by peristaltic contractions. FIGS. 16 to 17A illustrate cross sectional plan views of the retaining member of prior art devices and the consequences of peristaltic contractions by the rectal walls. The teachings of said figures are equally applicable to cases where the retaining member is a resilient ring, and where the retaining member is an inflatable cuff. In both cases, the retaining member presents a solid, continuous annular surface that resides against the rectal walls.

In FIG. 16 a retaining member 10 of the kind observed in prior art devices is in its fully expanded state, and assumes a uniformly circular (or substantially circular) shape. FIG. 16A demonstrates the effect of inwardly directed radial forces F along certain points on the circumference of said retaining member 10, in that portions of the resilient member on which inward forces F are directed, deform inwards, while other portions are correspondingly deformed outwards. Corresponding outward deformation of portions of retaining member 10 is a consequence of the solid and continuous annular structure of said retaining member 10. Where retaining member 10 is a resilient ring, the outward deformation is a consequence of the resilient properties of the constituting material. Where the retaining member 10 is an inflated cuff or balloon, the outward deformation is a consequence of relative incompressibility of air within the cuff or balloon, which applies corresponding pressure on other portions of the resilient member.

FIG. 17 illustrates retaining member 10 in its fully expanded state when disposed within the rectum. Adjacent rectal walls 94 are illustrated in a relaxed state, wherein no inwardly directed forces are applied on retaining member 10. In FIG. 17A the rectal walls 94 are illustrated undergoing a peristaltic contraction, wherein inwardly directed radial forces F are applied at various points on the circumference of retaining member 10. Since the inwardly directed compressive forces F are applied across the circumference of retaining member 10, said member 10 is forced to collapse inwardly into a series of substantially U-shaped deformations, with a view to reduce the circumferential surface area presented by retaining member 10 adjacent to rectal walls 94. The U-shaped deformations interfere with and reduce available lumen volume for passage of fecal matter through the retaining member. Simultaneously, such U-shaped deformations created gaps between rectal wall 94 and circumference of retaining member 10, through which fecal matter can pass, leading to seepage or leakage along the outside of the device.

In addition to the disadvantages set out above, it has generally been observed that prior art devices require a trained care provider to prescribe, insert, maintain and remove the device.

The applicant has recognized a need for a collection device for fecal discharge that addresses all of the above shortcomings, embodiments whereof are described herein.

SUMMARY OF THE INVENTION

The present invention is directed to a device that addresses the shortcomings in the prior art. A collector for fecal discharge having the features of the present invention comprises a self-expanding resilient collection component, a housing sheath and a transit component.

The collection component has an open proximal end, an open distal end and a lumen along the longitudinal axis of said component. The lumen provides a passage connecting the open proximal and distal ends. The collection component is constructed from a plurality of interconnected resilient arms that define spaces between the aims. The arms circumscribe the contour of the collection component. Adjacent arms within the collection component are resiliently biased away from each other so as to exert outwardly directed radial pressure. The outwardly directed radial pressure serves to expand the collection component and anchor it to rectal walls upon deployment within the rectum. The collection component is configured to exert radial pressure less than the pressure exerted by the adjacent rectal walls during peristaltic contractions.

The housing sheath has a flexible and resilient material overlaying one or both of the inner and outer contours of the collection component, without interfering with or blocking the open proximal and distal ends of said component and without interfering with or blocking the lumen connecting the open ends.

The transit component is a flexible substantially tubular sheath that provides a conduit for fecal discharge to migrate from the collection component to a receptacle. The transit component has a first open end, a second end, and a lumen connecting the two ends. The first open end of the transit component engages with the proximal end of the collection component.

The arms of the collection component may be pliant along the x, y and z axes. In accordance with a specific aspect of the invention, the arms of the collection component may have shape memory.

The arms of the collection component may circumscribe any one of a circular, substantially circular, cylindrical, substantially cylindrical, hemi-spherical, conical, frusto-conical, cup-shaped or funnel-shaped contour for the collection component.

In accordance with a particular aspect, the interconnected arms may form an undulating series of paired arms. Each pair of arms may be coupled to the two laterally adjacent pairs, and the first and last paired sets of arms may be coupled to each other to complete the contour of the collection component.

The interconnected arms may comprise a single continuous strand of resilient wire material arranged to circumscribe the contour of the collection component in an undulating configuration. In this aspect the free ends of said wire material are joined to complete said contour. In accordance with a particular aspect, said continuous strand of resilient wire material may be arranged in one or more torsion loops on one or more of the vertices formed by the peaks and troughs of the undulating wire material.

In another aspect of the invention, the interconnected arms of the collection component may be discrete, wherein adjacent arms are coupled to each other by connectors. In an more particular aspect adjacent arms of the collection component are coupled with resilient connectors that bias the coupled aims away from each other.

In an embodiment of the invention, arms of the collection component may be arranged in a series of crossed arm pairs arranged to circumscribe the contour of the collection component. The crossed arms within each pair are coupled at their respective longitudinal midpoints by a pivot pin. Free top and bottom ends of each crossed arm pair are coupled respectively to the adjacent free top and bottom ends of the laterally adjacent crossed arm pairs by pivot pins. The free top and bottom ends of the first crossed arm pair and free top and bottom end of the last crossed arm pair are coupled to each other to complete said contour.

The arrangement of arms circumscribing the contour of the collection component may be configured as a plurality of annular elements. The annular elements of the collection component have substantially identical contours and are coaxially aligned along the longitudinal axis of the collection component. Each annular element may be coupled to at least one adjacent element to achieve the contour of the collection component. In an embodiment, the elements are not coupled to each other, and are instead retained in longitudinal alignment relative to each other, by the housing sheath.

In another embodiment, the contour of the collection component may be frusto-conical, with the outer sidewall connecting the proximal end and distal end of the collection component at an outwardly directed angle of between 10° and 30° from the normal. The collection component may have fasteners to adhere to the rectal walls.

In an aspect of the invention, the expanded collection component may have an external diameter of between 20 mm and 60 mm. In another aspect, in its collapsed state, the collection component may have an external diameter of between 6 mm and 21 mm. In a further aspect the expanded collection component may have an internal diameter of between 20 mm and 40 mm at the open proximal end, and an internal diameter of between 20 mm and 60 mm at the open distal end. Yet more particularly, the expanded collection component may have an internal diameter of between 33 mm and 35 mm at the open proximal end, and an internal diameter of between 53 mm and 55 mm at the open distal end.

In an embodiment, length of the collection component may be between 10 mm and 50 mm.

In a specific embodiment of the invention, the outwardly directed radial pressure exerted by the collection component may be between 1 to 106 cm of $H_2O$. In a more specific embodiment, the outwardly directed radial pressure exerted by the collection component may be between 1 to 48 cm of $H_2O$. In another embodiment the outwardly directed radial pressure exerted by the collection component may be between 10 to 30 cm of $H_2O$, and in another embodiment may be 27.19 cm of $H_2O$.

The collection component may have one or more filaments attached thereto. Free ends of the one or more filaments are arranged to trail the proximal end of the collection component. In an embodiment, free ends of the one or more filaments may be arranged to have differing degrees of slack.

In a particular embodiment, the one or more filaments may be woven through the collection component in a drawstring arrangement. In a more specific embodiment, the filaments may be woven through vertices of the interconnected arms, which vertices are situated on one or both of the proximal end and distal end of the collection component.

Each trailing end of the filaments is housed within a corresponding rigid or semi-rigid longitudinal conduit and thereafter connected to a handle. Each conduit permits free movement of the residing filament along the direction of the conduit's longitudinal axis. One end of each conduit is located adjacent the proximal end of the collection component.

In an embodiment, the profile of the housing sheath corresponds with the profile of the collection component. In another embodiment, the material for the housing sheath is a polymeric material.

The second end of the transit component may be an open end having a connector thereon. The connector engages with the receptacle for fecal discharge. The second end of the transit component may alternatively be closed, which closed end serves as the receptacle for fecal discharge. In an embodiment the material for the flexible and resilient tubular sheath of the transit component is a polymeric material.

These and other embodiments, features and advantages will become apparent to a person of skill in the art when read in connection with the detailed description and accompanying drawings.

BRIEF DESCRIPTION OF THE DRAWINGS

FIG. 3 shows the expanded collection component of FIG. 2 wherein the trailing ends of the filament or thread are passed through piping or channels and thereafter connected to a handle.

FIG. 3A shows the compressed collection component of FIG. 2A wherein distal axial force applied to the trailing ends of the filament or thread is generated by pulling on the handle, and the unyielding surface against which vertices of said component abut is provided by the ends of the piping or channels proximal to said component.

FIGS. 4, 4A and 4B show the coiled or looped arrangement of the wire used to resiliently connect arms of the collection component.

FIGS. 4C to 4L show other arrangements for resiliently connecting arms of the collection component.

FIG. 12 shows a first embodiment of the insertion sleeve.

FIG. 13 shows an alternate embodiment of the insertion sleeve having selectively weakened wall portions.

FIG. 13A shows the embodiment of the insertion sleeve of FIG. 13, wherein said sleeve has been separated into two segments by application of opposing forces along the weakened wall portions.

DETAILED DESCRIPTION

The detailed description of the invention may be read with reference to the accompanying drawings. The drawings, which are not necessarily to scale, depict certain embodiments and are not intended to limit scope of the invention. The detailed description illustrates the invention by example, and not by limitation. The written description and drawings would enable the skilled person to make and use the invention.

The invention provides a collector of fecal discharge, for deployment within the rectum, said device comprising a collection component, a sheath for said collection device, a transit component and optionally, a separate receptacle, said collector configured to be deployed in the rectum. The collector additionally has a withdrawal mechanism for removal from the rectum. The invention further provides a system and apparatus for deployment of the collector of fecal discharge. The invention also addresses methods for deployment and withdrawal of said collector.

The collection component of the invention is a pliant self-expanding structure that adheres to the wall of the rectum with compliance selected to ensure that it anchors to the rectal walls and collapses and expands corresponding to movement of the adjacent anatomy during peristaltic contractions.

FIGS. 1 to 4L show specific embodiments of the collection component.

Figure 1:
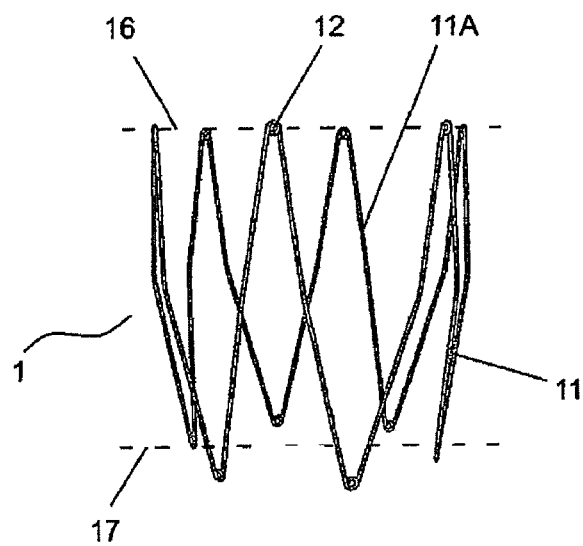
FIG. 1 shows a collection component in an expanded state.
Figure 1A:
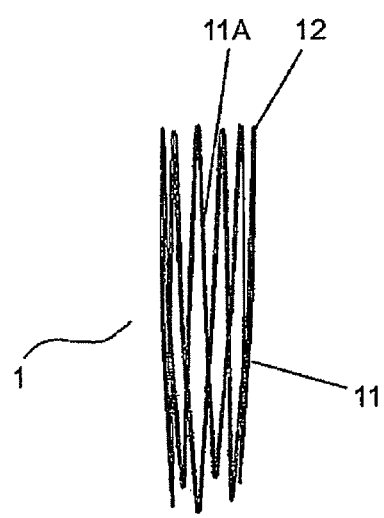
FIG. 1A shows the collection component in a compressed state.

FIGS. 1 and 1A depict an embodiment of self-expanding collection component 1 in its expanded and compressed states respectively.

The desired self-expanding and pliant properties of collection component 1 may be achieved by constructing said component using one or more of shape memory alloys, spring steel, stainless steel, thermoplastic polymers, and natural or synthetic material having elastic or resilient properties. Additionally, pliancy and resilience may be achieved by connectors—resilient and non-resilient—between various elements of the collection component 1, embodiments whereof are described herein.

In FIGS. 1 and 1A, collection component 1 is constructed from wire material 11 having shape memory. Collection component 1 in shown in an orientation where, upon deployment within the rectum, upper plane 16 (the "distal end") is situated distal to the anal opening, and lower plane 17 (the "proximal end") is situated proximal to the anal opening. For the purposes of this written description, reference to proximal and distal ends of various elements of collection component 1 are assumed to correspond to this orientation.

Collection component 1 may have any one of a circular or substantially circular, cylindrical or substantially cylindrical, hemi-spherical, conical, frusto-conical, cup-shaped or funnel-shaped contour, or such other contour as may be selected to correspond to the shape of the rectum. It would be understood by the skilled person that shape and configuration of collection component 1 may be selected so as to exert minimal and evenly distributed radial pressure on the adjacent rectal anatomy, with a view to minimize patient discomfort and to avoid risks of rectal necrosis. Shape and configuration of said component 1 is additionally selected with a view to ensure that component 1 does not suffer inelastic deformation or inelastic collapse.

Collection component 1 is constructed from an arrangement of arms 11A circumscribing (and accordingly defining the structural member having) the desired contour. The configuration of arms 11A along the contour of collection component 1 defines spaces ("interspaces") between adjacent arms 11A. Arrangement of arms 11A to circumscribe the desired contour of collection component 1 defines an open proximal end and an open distal end, and a lumen passing through said collection component 1 along the longitudinal axis and connecting said open proximal and distal ends. Upon application of inwardly directed radial forces upon collection component 1, arms 11A are forced closer to each other, thereby reducing the interspaces defined therebetween, and reducing the circumference and total surface area of the outside contour of collection component 1. The interspaces defined by the arrangement of arms 11A accordingly ensures that any part (or the whole) of collection component 1 may be compressed inwardly without effecting adjacent portions of said component 1, and without giving rise to u-shaped deformations that would serve to occlude the lumen of collection component 1. Further, the arrangement allows for inward compression of the whole or portions of collection component 1 without forcing portions of the outer contour of collection component 1 to separate from the adjacent anatomy.

The arm 11A—interspace arrangement of collection component 1 accordingly addresses two critical shortcomings of prior art devices wherein peristaltic contractions would cause the lumen of an indwelling component to be occluded by u-shaped deformations, while simultaneously giving rise to leakage of fecal discharge through gaps arising between the outer circumference of said indwelling component and adjacent rectal walls.

In FIGS. 1 and 1A, the anus 11A are arranged at a slant relative to the longitudinal axis of collection component 1 and are interconnected to form an undulating series of paired arms. Arms 11A within any pair may be connected to each other at one of the proximal or distal end thereby creating a vertex-like shape. In the embodiment shown, arms 11A within each pair are connected at the same end as in the remaining pairs. Further, each pair of arms is connected to the two laterally adjacent pairs of arms, to form a series of undulations. Depending on the preferred structure for the collection component 1, the undulations may be sinusoidal, zig-zag or an irregular series of alternating peaks and troughs. Paired arms are added to the structure and arranged to circumscribe the desired contour of collection component 1, wherein the single free end of the first paired set of anus and the single free end of the last paired set of arms are connected to complete the structure of the collection component 1.

The slant of arms 11A relative to the longitudinal axis of collection component 1 and the undulating structure of collection component 1 defines the interspaces between each arm 11A to allow for compression and expansion. The configuration, shape memory and resilient properties of the material selected for arms 11A and interconnections therebetween determine the pliancy, resilience, radial strength and self-expanding properties of collection component 1.

Figure 1B:
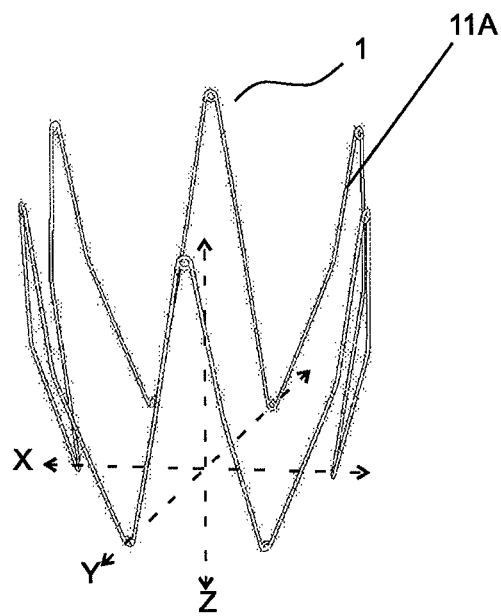
FIG. 1B shows the collection component in an expanded state with corresponding x, y and z axes superimposed thereon.
Figure 1C:
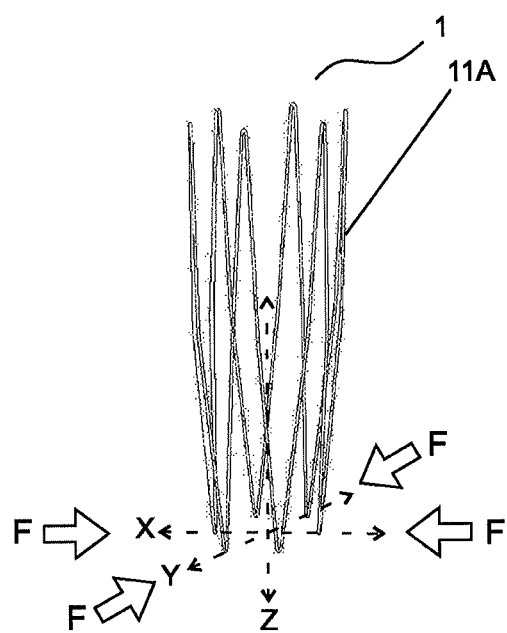
FIG. 1C shows compression of the collection component in response to inwardly directed radial forces directed along the x and y axes.
Figure 1D:
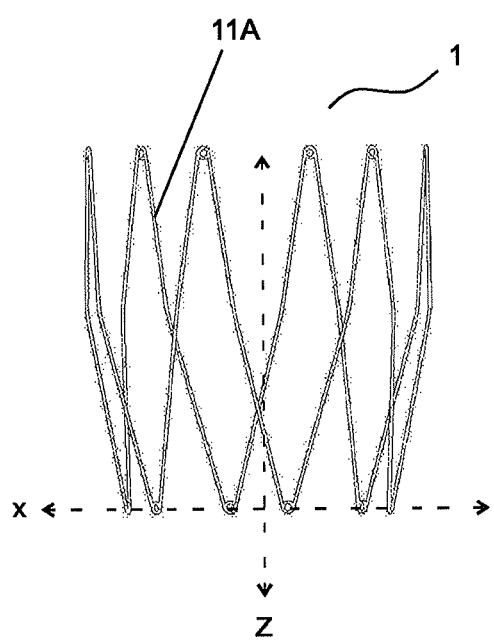
FIG. 1D shows the collection component in an expanded state with corresponding x, and z axes superimposed thereon.
Figure 1E:
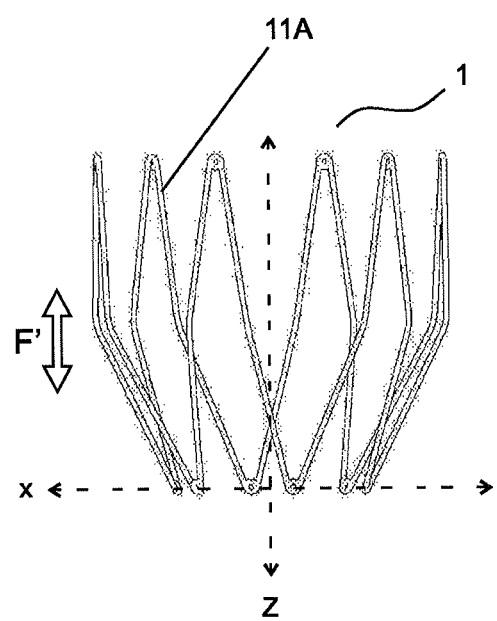
FIG. 1E shows compression of the collection component in response to longitudinally directed force along the z axis.

Arms 11A of collection component 1 may be independently pliant and resilient along all three axes. FIGS. 1B and 1C show collection component 1 in a fully expanded state and in a compressed state respectively, wherein in FIG. 1C inwardly directed radial forces F causes arms 11A and said collection component 1 to compress along the x and y axes. FIGS. 1D and 1E show collection component 1 in a fully expanded state and in a compressed state respectively, wherein in FIG. 1E inwardly longitudinally directed force F' causes arms 11A of collection component 1 to compress along the z axes. Upon termination of forces F or F', the resilient and shape memory properties of said arms 11A and connectors therebetween causes said arms 11A and said collection component 1 to revert to the expanded shape of FIG. 1B or 1D. It would be understood that while FIGS. 1B to 1D show compressive forces applied along a maximum of any two axes of collection component 1, said forces may be applied simultaneously along all three axes, and the individual arms 11A and collection component 1 would still compress and expand in the manner illustrated.

The compressive and expansive properties of collection component 1 and its structural arms 11A in response to inwardly directed radial forces F along the x and y axes allows said component 1 to expand and contract in response to expansions and contractions of adjacent rectal walls, thereby ensuring that collection component 1 adheres to rectal walls.

The compressive and expansive properties of collection component 1 in response to inwardly directed longitudinally forces F' allows said component 1 to expand and contract in response to pressure exerted by folds of tissue and wrinkles on the inner surface of the rectal walls, against which portions of collection component 1 (particularly vertex portions thereof) abut, without allowing such movement to dislodge component 1 from its position relative to the rectum.

Figure 18:
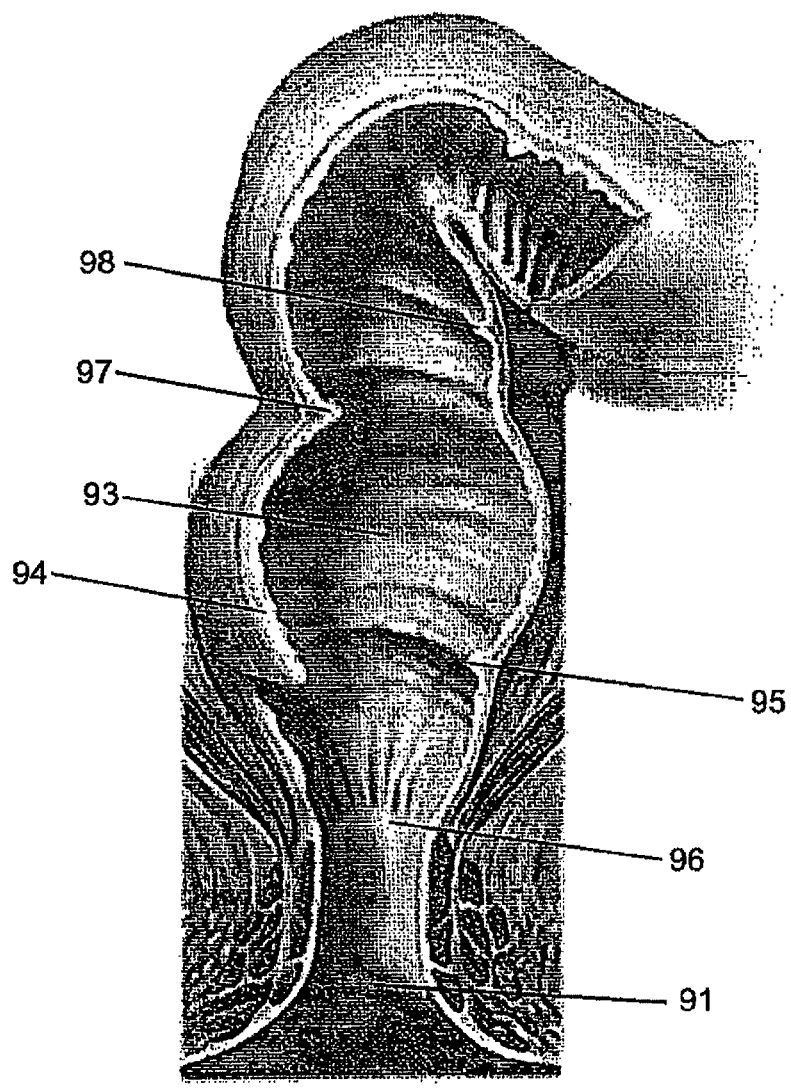
FIG. 18 shows the internal physiology of the rectum.

FIG. 18 illustrates certain portions of the rectum 93. Typically, upon insertion in the rectum, some or all parts of proximal or distal ends of collection component 1 may abut against folds of tissue and/or wrinkles found on the inner surface of the rectal walls 94. In certain cases, such abutment may be against the first transverse fold 95 or the second transverse fold 97 of the rectum. Peristaltic contractions, or other muscular movement may cause said folds or wrinkles to bear against the collection component 1, thereby applying inwardly directed longitudinal force against component 1, in response to which said component 1 would compress along its longitudinal axis, without being dislodged relative to the rectum. Upon termination of application of said force, collection component 1 resumes its original shape as a consequence of the resilient and shape memory properties of its arms 11A.

It would be understood that the configuration of collection container 1 as described above can be achieved in a number of different ways. In the embodiment shown in FIGS. 1 and 1A, configuration of collection component 1, arms 11A and interconnection between said arms 11A is achieved by arranging a continuous strand of wire material 11 having shape memory characteristics in an undulating configuration, and joining the ends of said wire material 11 to impart a substantially cylindrical or frusto-conical contour to the wire arrangement. At one or more of the vertices of the undulating wire arrangement, wire material 11 may be configured to have at least one loop or coil 12, which loop or coil 12 acts as a torsion spring to provide additional shape memory and pliancy to collection component 1.

Front, side and perspective views of a single loop coil arrangement are provided in FIGS. 4, 4A and 4B respectively. While the embodiments illustrated in FIGS. 4, 4A and 4B show only a single loop or coil at each vertex, a plurality of loops or coils could be provided—the number of loops or coils at each vertex 12 being selected based on the desired torsional resilience.

Collection component 1 may also be constructed without any loops or coils 12, and may rely entirely on shape memory and elastic properties of the underlying material of arms 11A for the desired resilience and pliancy to ensure that in its expanded state, said component 1 adheres to adjacent rectal walls. In an embodiment, some or all parts of collection component 1 may have a polymeric material coated or otherwise affixed thereon for improved cushioning and adherence.

In a preferred embodiment, 0.3 to 2.0 mm medical grade stainless steel wire is used for constructing the arms 11A of collection component 1, which provides significant radial strength and was found to improve adherence of said component 1 to the rectal walls, while minimizing the likelihood of injury, trauma or involuntary migration of said component 1. In a particularly preferred embodiment 0.7 mm medical grade stainless steel wire may be used for constructing said arms 11A. In a yet more preferred embodiment said wire material is medical grade 316 stainless steel wire.

The ends of the underlying material for arms 11A may be joined to each other using a variety of methods that would be immediately apparent to a person of skill in the art. In a preferred embodiment, butt joints or lap joints may be used.

In another embodiment, arms 11A of collection component 1 are discrete arms having shape memory characteristics and connected to each other by connectors, in an undulating configuration.

Arms 11A may be connected to circumscribe any one of a circular or substantially circular, cylindrical or substantially cylindrical, hemi-spherical, conical, frusto-conical, cup-shaped or funnel-shaped contour, or such other contour as may be appropriate to conform to shape of the rectal walls.

Connectors used to connect the discrete arms 11A may comprise any one of a variety of mechanisms that would be immediately apparent to a person of skill in the art, with a view to ensuring pliancy and resilience of collection component 1. Embodiments of various connectors and are illustrated in FIGS. 4C to 4J.

Figure 4C:
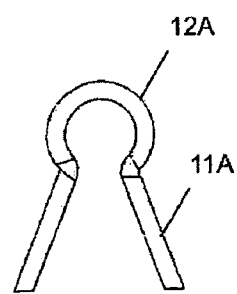
Figure 4D:
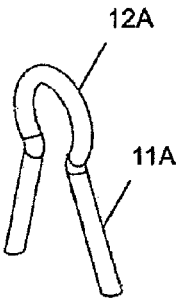

FIGS. 4C and 4D show front and perspective views of an embodiment where adjacent arms 11A are connected with a C-shaped loop 12A, wherein loop 12A and two adjacent arms 11A may be formed from a single material as a continuous piece, or alternately from a plurality of elements joined together, wherein said plurality of elements may be manufactured using the same underlying material or different materials. The material for C-shaped loop 12A may be selected based on the desired shape memory, resilience, radial strength and pliancy.

Figure 4E:
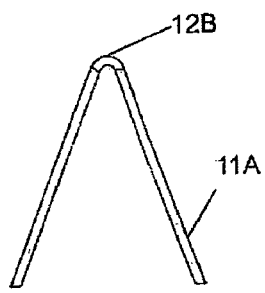
Figure 4F:
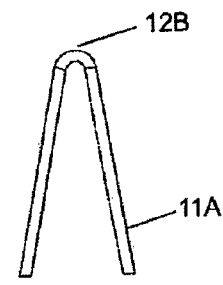

FIGS. 4E and 4F show front and perspective views of an embodiment where adjacent arms 11A are connected at the vertex with a substantially u-shaped or substantially v-shaped connection 12B. Connection 12B and two adjacent arms 11A may be formed from a single material as a continuous piece, or alternately from a plurality of elements joined together, wherein said elements may be manufactured using the same underlying material or different materials. The material for the connection 12B may be selected based on the desired shape memory, resilience, radial strength and pliancy.

FIGS. 4G to 4J show embodiments where adjacent arms 11A are connected with a cylindrical pin or pivot pin arrangement 12C, and a resilient connector 12D, 12E interposed between the two arms 11A. The resilient connector serves to push arms 11A apart from each other, causing collection component 1 to have self-expanding characteristics.

Figure 4G:
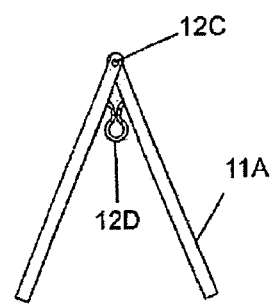
Figure 4H:
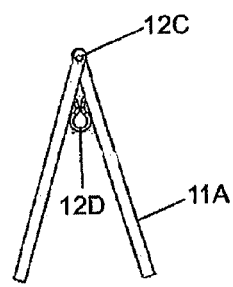

FIGS. 4G and 4H show a front view and a perspective view of an embodiment wherein resilient connector 12D comprises arms having a c-shaped loop wherein each arm of said connector 12D is connected to one of the two adjacent arms 11A.

FIGS. 4I and 4J show front and perspective views of an embodiment wherein resilient connector 12E comprises a compression spring, each end of said spring 12E connected to one of adjacent arms 11A.

It would be understood that in addition to the specific embodiments of resilient connector 12D, 12E discussed herein, any other object with shape memory or resilient properties may be used to cause adjacent arms 11A to move apart from each other, thereby causing collection component 1 to expand.

FIGS. 4K and 4L show a configuration for a particular embodiment of collection component 1 wherein arms 11A' are connected to each other in a collapsible scissor arrangement.

In FIG. 4K, arms 11A' are arranged in a series of crossed pairs, wherein crossed arms 11A' within each pair are connected at their respective longitudinal midpoints (or substantially their longitudinal midpoints) using connectors that permit rotational movement. In a preferred embodiment said connectors comprise cylindrical pins or pivot pins 12G. The free top and bottom ends of crossed arms 11A' on each side of a crossed pair is connected respectively to the adjacent free top and bottom ends of crossed arms 11A' of the next crossed pair. Said free top and bottom ends are connected to each other using connectors that permit rotational movement. In a preferred embodiment said connectors comprise cylindrical pins or pivot pins 12C'.

Crossed pairs of arms 11A' are added to the structure and arranged to circumscribe the desired contour of the collection component 1, wherein a free top and bottom end of the first crossed pair of arms 11A' and the free top and bottom end of the last crossed pair of arms 11A' are connected to complete the structure of the collection component 1.

The arrangement of crossed pairs of arms 11A' creates a network of crossed arms with diamond shaped and triangular interspaces defined therebetween. Said arrangement creates a collapsible scissor configuration, which allows for compression and expansion of collection component 1. The configuration, shape memory and resilient properties of the material selected for the arms 11A' determines the pliancy, resilience and self-expanding properties of collection component 1.

FIGS. 4K and 4L show a section of the collapsible scissor arrangement in an expanded and collapsed state respectively. In a preferred embodiment, the interconnected top and bottom ends of each set of adjacently placed crossed pairs of arms 11A' are connected to each other by a resilient connector. In a preferred embodiment resilient connector 12F is a tension spring or an extension spring. As shown in FIG. 4L, application of inwardly directed radial forces causes adjacent crossed pairs of arms to move closer to each other in a lateral direction, correspondingly moving the top and bottom ends of said crossed pairs away from each other. The increase in distance between the top and bottom ends places an axial load upon resilient connector 12F. Upon termination of application of inwardly directed radial compression, resilient connector 12F resumes its relaxed position, thereby bringing the top and bottom ends of adjacent crossed pairs of arms 11A' closer to each other, and correspondingly increasing the interspaces defined between adjacent crossed pairs. Said movement causes collection component 1 to move towards and attain its expanded state.

As in the earlier embodiment, interspaces defined between arms 11A' of collection component 1 allows said arms to move closer to each other upon application of inwardly directed radial forces. Said movement reduces the circumference and total surface area of the outside contour of collection component 1. The reduction in circumference ensures that any part (or the whole) of collection component 1 may be compressed inwardly without effecting adjacent portions of said component 1, and without giving rise to u-shaped deformations that would serve to occlude the lumen of collection component 1. This additionally avoids the corresponding formation of spaces between the outer contour of collection component 1 and the adjacent rectal walls, and the consequent problem of leakage.

Figure 4M:
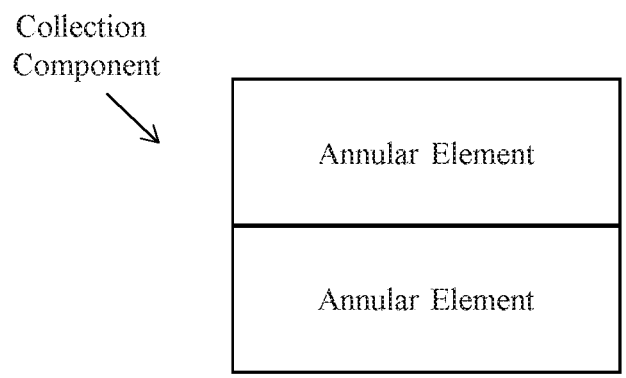
FIG. 4M shows a schematic of annular elements of the collection component having substantially identical contours that are coaxially aligned along the longitudinal axis of the collection component.
Figure 4N:
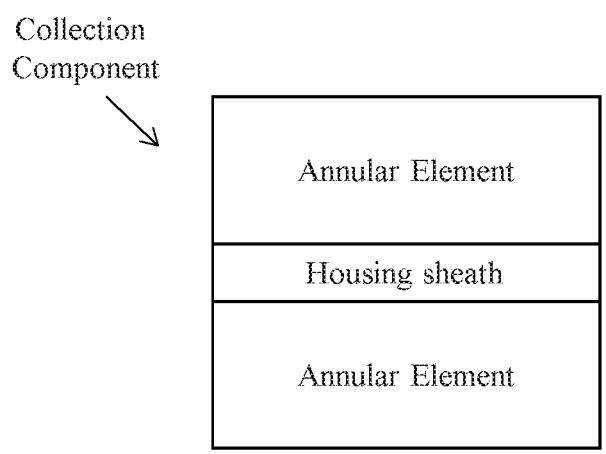
FIG. 4N shows a schematic of annular elements that are not coupled to each other, and are instead retained in longitudinal alignment relative to each other, by the housing sheath.

In an embodiment of the invention, the arrangement of arms circumscribing the contour of collection component 1 may be configured as a plurality of annular elements each having a cylindrical, substantially cylindrical or frusto-conical contour. The contours of said plurality of annular elements are substantially identical, and said elements are aligned along the longitudinal axis of the collection component (as shown in FIG. 4M). Each annular element may be resiliently or otherwise coupled to the immediately adjacent annular element to achieve the desired size and contour of collection component 1. It would be understood that each annular element may be configured in any of the arm—interspace arrangements disclosed in connection with the collection component as a whole. In another embodiment, annular elements are not coupled to each other, and are instead retained in longitudinal alignment relative to each other, by the housing sheath (as shown in FIG. 4N).

It would be understood that in addition to the specific embodiments and configurations for the arms, connectors and resilient connectors discussed herein, any other elements or components with the desired shape memory or resilient properties may be used to cause collection component 1 to expand and contract in an efficient manner. Other mechanisms that may be used to impart self-expanding properties included hydraulically actuated mechanisms, pneumatically actuated mechanisms and magnetically actuated mechanisms.

Collection component 1 relies on its pliant and self-expanding properties to ensure that its outer circumference adheres to adjacent rectal walls, thereby anchoring said collection component 1 to said rectal walls when the rectum is relaxed, and also during peristaltic contractions. The circular, substantially circular, cylindrical, substantially cylindrical, hemi-spherical, conical, frusto-conical, cup-shaped or funnel-shaped contour, allows the outer contour of collection component 1 to correspond better to the adjacent anatomy of the rectum. Moreover, the increased surface area provided by the selected configurations in comparison to a ring like retainer device, ensures better anchoring properties.

Simultaneously, providing for interspaces defined between the arrangement of structural arms 11A, 11A' of collection component 1 allows for contraction of said component 1 without occlusion of the lumen therethrough and without separating the outer contour from adjacent rectal walls.

In addition to the above, the independent pliancy of each arm 11A, 11A' and of collection component 1 as a whole along all three axes ensures that the incontinence device does not interfere with peristaltic contractions, and with the corresponding effectiveness of the fecal discharge process. Additionally, the ability of the collection component to expand and collapse corresponding to movement of the adjacent anatomy prevents the peristaltic contractions of the rectal walls and tissue folds from dislodging the collection component from the desired location and forcibly expelling it towards the anal opening.

Another advantage of having a collection component that expands and collapses corresponding to movement of the adjacent anatomy is avoidance of continual outwardly directed radial force on rectal tissue, that could eventually cause one or more of rectal tissue aggravation, mucosal damage, rectal stenosis, degeneration of the internal or external nerves, rupture of the superior rectal blood vessels, and damage to the internal or external sphincter leading to permanent dysfunctioning of the sphincter. The compliant collection component 1 additionally significantly reduces foreign body sensation and patient discomfort.

In a preferred embodiment, collection component 1 has a frusto-conical contour, wherein the outer sidewall connecting the proximal end and distal end is at an outwardly directed angle of between 10° and 30° from normal. Said configuration provides an optimal shape for collection component 1 to adhere to the rectal walls at the desired location, eliminates the risk of involuntary inward migration, and contributes to trauma free withdrawal. In a particular embodiment, collection component 1 may have fasteners to assist in adhering to the anatomy of the rectum, including inter alia adhesives, hooks, clips, catches and clasps.

In the expanded state of an embodiment, collection component 1 may have an external diameter of between 30 mm and 60 mm. The external diameter of said collection component in a fully collapsed embodiment may lie between 6 mm to 21 mm.

In an embodiment, collection component 1 has a frusto-conical configuration wherein internal diameter at the proximal end 17 is between 30 mm and 40 mm, and internal diameter at the distal end 16 is between 50 mm and 60 mm. In another embodiment, collection component 1 has a frusto-conical configuration wherein internal diameter at the proximal end 17 is between 33 and 35 mm, and internal diameter at the distal end 16 is between 53 mm and 55 mm.

It would be understood that the longitudinal dimension of collection component 1 may be selected based on patient physiology, desired resilience and state of the rectal walls. However, in a preferred embodiment, collection component 1 measures between 2 cm to 5 cm in length along the axial direction, which provides sufficient anchorage against the rectal walls, without causing said component 1 to abut against the anorectal junction 96.

Clinical studies have demonstrated that empty rectum pressure of incontinent persons is between 0 to 14 cm of $H_2O$. The pressure range at which persons first feel a sensation of rectal filling is between 6 to 48 cm of $H_2O$. The maximum tolerable pressure that a person is likely to tolerate before feeling an irresistible and painful urge to allow fecal discharge is 106 cm of $H_2O$.

Based on these studies, it has been discovered that the full range of outward radial pressure that may be exerted collection component 1 on adjacent rectal walls is between 1 to 106 cm of $H_2O$. In a preferred embodiment, outward radial pressure exerted by collection component 1 on the adjacent rectal walls is between 1 to 48 cm of $H_2O$. In a more preferred embodiment, outward radial pressure exerted by collection component 1 on the adjacent rectal walls is 27.19 cm of $H_2O$. Said radial pressures have been selected with a view to minimize patient discomfort and foreign body sensation, while allowing collection component 1 to anchor against the rectal walls and expand and contract in response to peristaltic contractions.

Collection component 1 may be annealed using optimized parameters resulting in optimal radial strength and device finish.

The invention presents a significant improvement over prior art devices of the indwelling catheter type in that such prior art devices are either deployed (or forced by peristaltic contractions) to abut against the shelf provided by the anorectal junction 96 (FIG. 18), which abutment prevents the device from being expelled entirely from the rectum. Owing to the somatic nerves in the area, devices abutting the anorectal junction 96 cause acute foreign body sensation and patient discomfort. Additionally, ensuring that such devices are retained within the rectum is dependent on sphincter tone of an individual—in cases where sphincter muscles of an individual are weak, the anorectal junction 96 fails to provide a suitable abutment surface to maintain prior art devices in position, leading to involuntary ejection of the device from the rectum.

Collection component 1 of the present invention however, is capable of anchoring to the rectal walls as a result of its configuration and pliancy. Said component 1 therefore does not rely on the shelf of the anorectal junction 96 to maintain its location relative to the rectum. As a result, collection component 1 can be deployed and retained higher within the rectum, and preferably above the anorectal junction 96 and below the first transverse fold 95 or second transverse fold 97 therewithin. In an embodiment, collection component 1 may be deployed below the third transverse fold 98. Since nerves in this area are visceral and not somatic, the patient is only aware of pressure sensations, and not pain sensations in connection with presence of collection component 1. Further since collection component 1 is configured to be compliant with contractions of the adjacent rectal anatomy, even the pressure sensation is largely absent, leading to a significantly reduced foreign body sensation and higher patient tolerance for the device.

Figure 2:
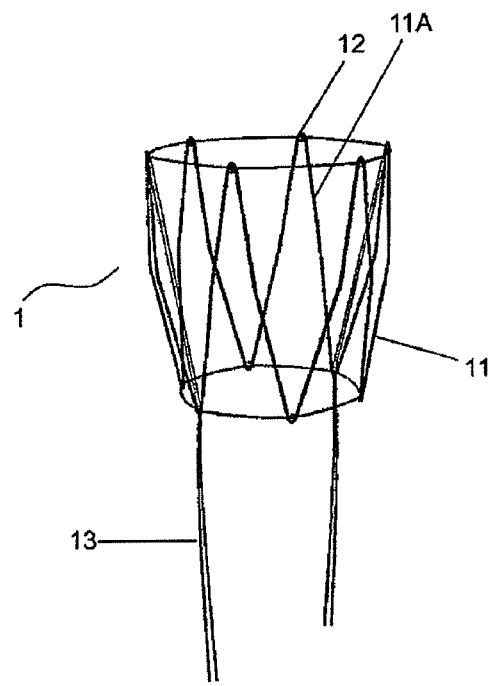
FIG. 2 shows the collection component in an expanded state, having a filament or thread woven through its vertices with trailing ends.
Figure 2A:
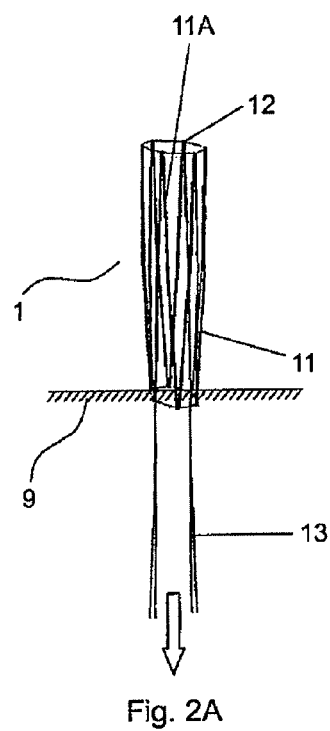
FIG. 2A shows the collection component in a compressed state, wherein inwardly directed radial forces for compression are generated by axial force applied to the trailing ends of the filament or thread in a direction distal to said component, and simultaneous abutment of the vertices of the component against an unyielding surface.

FIGS. 2 and 2A show an embodiment of collection component 1 having at least one filament or thread 13 woven or passed through vertices on its proximal end 17 and distal end 16, and having the free ends of said filament or thread 13 trailing said proximal end 17. In an embodiment the filament or thread 13 may be woven around the collection component in a drawstring arrangement, wherein simultaneously pulling on the free ends of the filament or thread causes distal end 16 and proximal end 17 to contract, and for said component 1 to collapse. In the embodiment shown in FIGS. 2 and 2A, filament or thread 13 is woven to pass through each vertex 12 of collection component 1 at least once. However, other arrangements to ensure an appropriate drawstring configuration would be immediately apparent to the skilled person.

FIG. 2 shows collection component 1 in its fully expanded state, having no inwardly directed radial forces acting upon it, such as when the rectal walls to which it adheres are in a relaxed state.

FIG. 2A shows collection component 1 in a collapsed state for withdrawal from the rectum through the anal canal, wherein the inward radial forces required for compression are generated by applying an axial force to the trailing ends of the filament or thread in the direction moving from distal end 16 to proximal end 17 of said component 1 ("proximal direction"), and simultaneous abutment of vertices 12 located at proximal end 17 of said component 1 against an unyielding surface 9 (which unyielding surface may be provided by a care provider's hand gripping the proximal end 17). Abutment of proximal end vertices 12 against unyielding surface 9 prevents premature movement of collection component 1 in the proximal direction, while axial force applied to the thread or filament 13 in the proximal direction causes distal 16 and proximal 17 ends of collection component 1 to contract and for said component 1 to eventually collapse completely.

In an embodiment, the configuration of collection component 1 and the drawstring arrangement of thread or filament 13 are chosen to ensure that collection component 1 collapses sequentially. In a particular embodiment, the collection component 1 and drawstring arrangement of thread or filament 13 is configured so that the sequence of collapse ensures closing of substantially 70% of distal end 17, followed by substantially 100% of proximal end 16, and in turn followed by collapse of the remaining substantially 30% of distal end 17. Sequential collapse serves to reduce possible trauma (tissue pinching) arising from collapse, and prevents accidental soiling when collection component 1 is withdrawn. Sequential collapse of collection component 1 may be achieved by providing differing degrees of slack to each trailing end of thread or filament 13. Upon application of proximally directed axial force to trailing ends of thread or filament 13, the portion of collection component 1 linked to the trailing end having less slack will collapse first, while the portion of said component 1 linked to the trailing end having more slack will collapse only after the additional slack is completely exhausted by the proximally directed axial force.

In FIGS. 3 and 3A trailing ends of filament or thread 13 are passed through rigid or semi-rigid pipes or conduits 14 and are thereafter connected to handle 15. Pipes or conduits 14 are selected with an internal diameter that permits free movement of filament or thread 13 residing within. Other criteria for selecting shape, configuration and construction material for said pipes or conduits 14 include inter alia minimizing foreign body sensation and sphincter dysfunction.

FIG. 3 shows collection component 1 in its expanded state. In FIG. 3A, collection component 1 is collapsed by applying to handle 15, an axial force in the proximal direction, which axial force is transmitted through handle 15 to filament or thread 13. The rigid or semi-rigid pipes or conduits 14 are prevented from moving in a proximal direction by the hand simultaneously gripping them. Abutment of proximal end vertices 12 of collection component 1 against unyielding surface 9—provided by the adjoining ends of the pipes or conduits 14—prevents movement of said collection component 1 in the proximal direction, while tension applied to thread or filament 13 causes distal 16 and proximal 17 ends of said component 1 to contract, and eventually for the component 1 to collapse completely.

In a preferred embodiment, the thread or filament 13 may provide a visual indication when collection component 1 has been completely collapsed. In another embodiment, the thread or filament 13 and handle 15 may be configured to provide audible or tactile feedback when collection component 1 has been completely collapsed. The thread or filament 13 and handle 15 may further be provided with a locking or ratchet mechanism to prevent collection component 1 from resuming its expanded state, by preventing said thread or filament 13 from being withdrawn into conduits 14.

Figure 5:
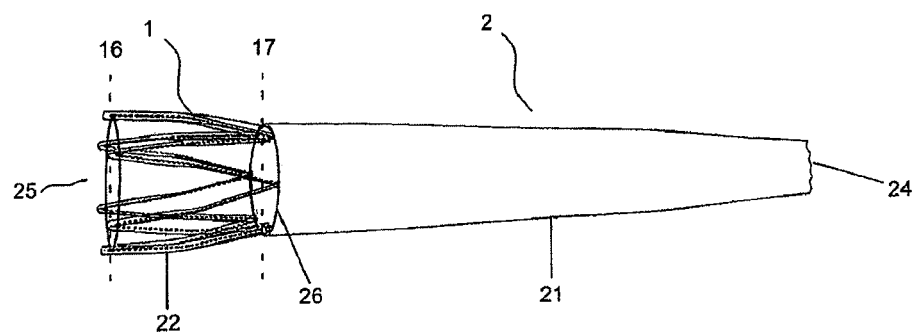
FIG. 5 shows an assembled internal component having the collection component housed within a sheath, and a transit component affixed to an end of the sheath.
Figure 5A:
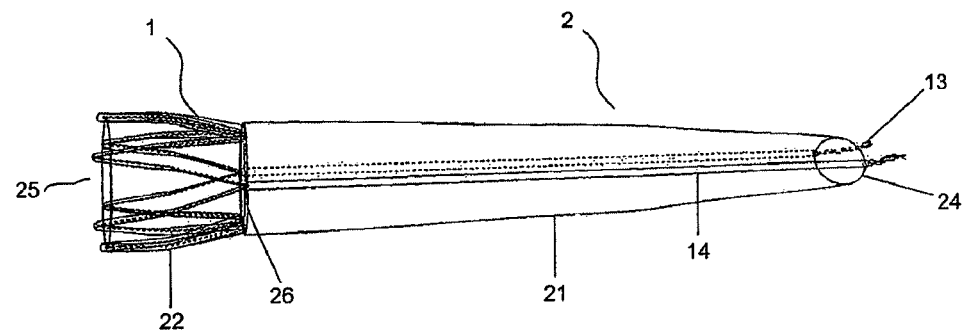
FIG. 5A shows the assembled internal component of FIG. 5, the collection component having a filament or thread woven through its vertices, wherein the trailing ends of said filament or thread pass through piping or channels, said piping or channels being housed within the transit component.
Figure 5B:
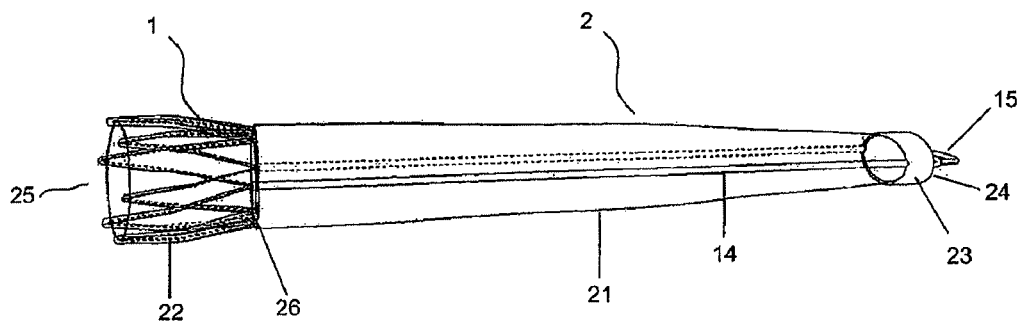
FIG. 5B shows, the assembled internal component of FIG. 5A wherein trailing ends of said filament or thread are affixed to a connector and handle.
Figure 5C:
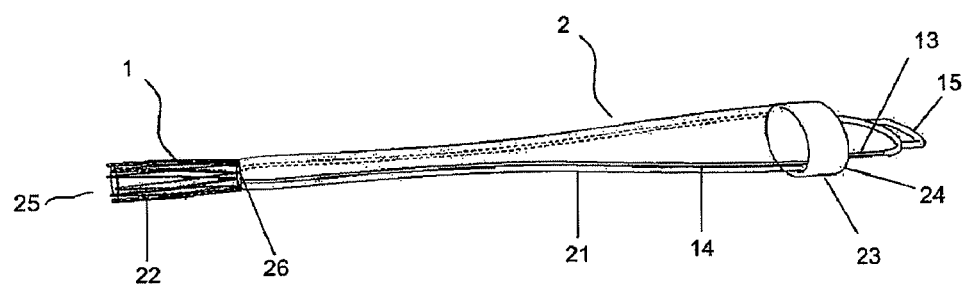
FIG. 5C shows the assembled internal component of FIG. 5B wherein the collection component is compressed by application of a distally directed axial force applied to the trailing ends of the filament or thread by pulling on the handle, and simultaneous abutment of the bottom vertices of the collection component against the unyielding ends of the piping or channels proximal to said collection component.

FIGS. 5 to 5C show embodiments of collection component 1 having a sheath and transit component 21 affixed thereto.

FIG. 5 shows an assembled internal component 2 comprising collection component 1 housed within a thin, skin or tissue friendly housing sheath 22, and having a transit component 21 affixed to its proximal end. Collection component 1 housed within said housing sheath 22 adheres resiliently to the rectal walls. Distal end 16 of said collection component 1 provides an opening 25 to funnel fecal discharge into the lumen through said component 1 into and onwards through transit component 21.

Housing sheath 22 for collection component 1 overlays at least one of the inner or outer contour of component 1, while maintaining the open proximal and distal ends of component 1 and patency of the lumen connecting said open ends. Housing sheath 22 assists in hosting, cushioning, blunting impact of, adhering, sealing and tapering of said component 1. Housing sheath 22 may be constructed of any one or more of a variety of materials chosen inter alia for bio-compatibility, effectiveness in minimizing foreign body sensation, reduction of tissue irritation and damage, pliancy and adherence with rectal walls, structural strength, flow, bonding, and leak-proof and seepage resistant properties. In a particular embodiment housing sheath 22 may be a polymer sheath. In a preferred embodiment housing sheath 22 comprises a semi-crystalline polymer. The polymeric material may be cross-linked or non cross-linked and may be chosen with an orientation that would improve tear properties.

Housing sheath 22 may be configured such that its profile at distal end 16 of collection component 1 corresponds substantially to the profile of distal end 16 of said collection component 1. In the embodiment of collection component 1 shown in FIGS. 1 and 1A, profile of housing sheath 22 may be configured to substantially correspond and adhere to the undulating circumferential configuration of collection component 1 at distal end 16. In the embodiment of collection component 1 shown in FIGS. 4K and 4L, the profile of housing sheath 22 may be configured to substantially correspond and adhere to the profile of distal end 16 of the scissor configuration.

In another embodiment of collection component 1 shown in FIGS. 4K and 4L, the housing sheath 22 may consist of material with elastic properties, which properties bias the collection component towards its expanded state in the same manner as resilient connector 12F.

The configuration of housing sheath 22 minimizes and reduces seepage of fecal matter from the edges of collection component 1 both in its expanded and collapsed states and also reduces impacting of fecal matter in comparison to an arrangement where a sheath presents a circular circumference at distal end 16. Said construction and configuration of housing sheath 22 also reduces the likelihood of involuntary forward migration, or accidental dislodgement of collection component 1 as a consequence of stool impacting against a continuously circular circumferential arrangement.

Other mechanisms that may be incorporated for reducing seepage of fecal matter from the edges of collection component 1, and for improving transit of solid stool from collection component 1 through transit component 21, include inter alia vacuum suctioning and grinding.

In an embodiment, housing sheath 22 is uncoated and without any surface additives. In another embodiment, at least one of the outside and inside surfaces of housing sheath 22 may be coated. Coatings for housing sheath 22 may be selected from the group of hydrophilic, hydrophobic, friction enhancing, friction reducing, antimicrobial, anesthetic and anti-inflammatory coatings. The outside and inside surfaces of housing sheath 22 may have the same or different coatings, single or multiple coatings, and on single or multiple locations to enhance desired behavior and properties.

Transit component 21 also comprises a thin, skin friendly substantially tubular sheath having at least one open end, and having a lumen passing therethrough, connecting said at least one open end to the other end. As in the case of housing sheath 22, use of a compressible sheath for the transit component 21 residing in the rectum and anal canal allows the anal sphincter to function in a normal fashion, thereby reducing or negating manifestation of anal sphincter dysfunction. Additionally, use of a thin sheath as transit component 21 allows said transit component 21 to be compressed by contractions of the rectal walls, anal canal and anal opening, thereby preventing patient discomfort, tissue necrosis and degeneration of muscle tone leading to sphincter dysfunction.

Selection of appropriate sheath material for transit component 21 improves 'patient-friendliness' of the device by reducing the magnitude of foreign body sensation and resulting discomfort that a patient may experience. Characteristics on which selection of said sheath material for transit component 21 is based include bio-compatibility, effectiveness in minimizing foreign body sensation, reduction of tissue irritation and damage, pliancy and adherence with the rectal walls, structural strength, flow, bonding, and leak-proof and seepage resistant properties.

In a particular embodiment the sheath for transit component 21 may be a polymer sheath. In a preferred embodiment said sheath for transit component 21 comprises a semi-crystalline polymer. The polymeric material may be cross-linked or non cross-linked and may be chosen with an orientation that would improve tear properties. In a preferred embodiment, characteristics for selection of the polymeric material include inter alia the orientation of the semi-crystalline polymer, its extrusion process, surface characteristics such as lubricity, antimicrobial, hydrophilic, and anesthetic properties, are selected to reduce patient discomfort and opportunities for accidents or unfavorable outcomes, and also to enable a health care provider to care for the patients in an efficient manner.

In an embodiment, transit component 21 is uncoated and without any surface additives. In another embodiment, at least one of the outside and inside surfaces of transit component 21 may be coated. Coatings for said transit component 21 may be selected from the group of hydrophilic, hydrophobic, friction enhancing, friction reducing, antimicrobial, anesthetic and anti-inflammatory coatings. The outside and inside surfaces of said transit component 21 may have the same or different coatings, single or multiple coatings, and on single or multiple locations to enhance desired behavior and properties. The coatings on transit component 21 may be same or different from coatings on housing sheath 22.

The structure of transit component 21 may take different geometrical shapes, dimensions and configurations. Said transit component 21 may have natural or non-natural conduits, which house other components that are relevant for withdrawal of collection component 1. Transit component 21 may also have internal activation or trigger mechanisms to flush or evacuate contents.

The at least one open end 26 of transit component 21 is affixed to housing sheath 22 at proximal end 17 of collection component 1, such that fecal discharge funneled into opening 25 of collection component 1 in turn passes through transit component 21. In an embodiment the other end 24 of said transit component is also open and provides an outlet for fecal discharge into a receptacle, container or compartment. In another embodiment, transit component 21 is closed at said other end 24 thereby providing a tubular receptacle for fecal discharge.

FIG. 5A shows assembled internal component 2, comprising collection component 1 housed within housing sheath 22, having one end 26 of transit component 21 affixed to its proximal end 17, and having a filament or thread 13 woven through its top and bottom vertices in a drawstring arrangement, wherein trailing ends of said filament or thread 13 pass through piping or conduits 14, wherein said piping or conduits 14 are housed within transit component 21.

FIG. 5B shows an embodiment of assembled internal component 2 wherein transit component 21 has a ring or connector 23 at end 24 that serves as an interface to a receptacle, containment device or compartment. The embodiment additionally has handle 15 to which the trailing ends of filament or thread 13 are attached.

FIG. 5C illustrates voluntary collapse of collection component 1 in assembled internal component 2, by application of an axial force applied to handle 15 in the proximal direction, the mechanism for which is explained above.

In an embodiment of the invention, at least one of collection component 1 and transit component 21 include odor neutralizers for discharges from the rectum, including by way of contact or passage of such discharges through one or more odor neutralizing substances such as inter alia ammonia gas, ground coffee beans, camphor, lime quartz and charcoal. Odor neutralizing substances may be provided by way of coatings on internal surfaces of housing sheath 22 or of transit component 21.

In an embodiment, assembled internal component 2 may be attached to appropriate valve arrangements and collection devices through the connectors or interfaces illustrated.

FIGS. 6, 6A, 6B, 7, 8 and 12 show components for, and an embodiment of, a device for insertion of assembled internal component 2 into the rectum.

Figure 6:
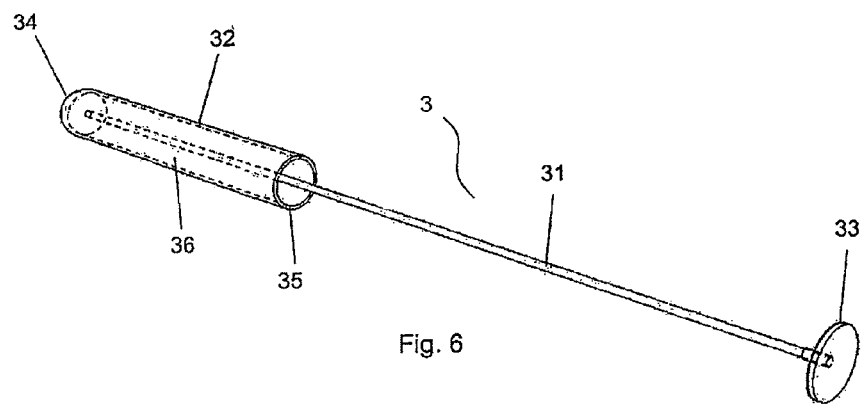
FIG. 6 shows a plunger for an insertion device.

FIG. 6 shows a plunger 3 for the insertion device. Plunger 3 comprises a rigid or semi-rigid insertion rod 31 having a base 33 and a head 32. Base 33 provides a flat surface for application of pressure to advance plunger 3 or for gripping to withdraw the plunger. In the embodiment shown, head 32 is cylindrical with an open end 35 proximal to base 33, and with a capped end 34 distal from base 33. Capped end 34 may have a blunt rounded tip to facilitate insertion through the anal opening into the rectum without protruding, scratching, entangling or any other manner of tissue or skin trauma. Open end 35 provides access to cavity 36 within head 32. Cavity 36 may extend partially or substantially through head 32.

Head 32 may be constructed from a variety of inert or biocompatible materials, including inter alia a soft, derma-tissue friendly material. Further, said head 32 may be shaped so as to facilitate smooth, non-traumatic insertion and removal. Head 32 may have one or more coatings, a secondary substrate or substrates on its external surface, which improve lubricity while reducing tissue trauma and patient discomfort.

In a preferred embodiment, the cross-sectional profile of head 32 is small, and selected with a view to reduce trauma and foreign body sensation.

Figure 6A:
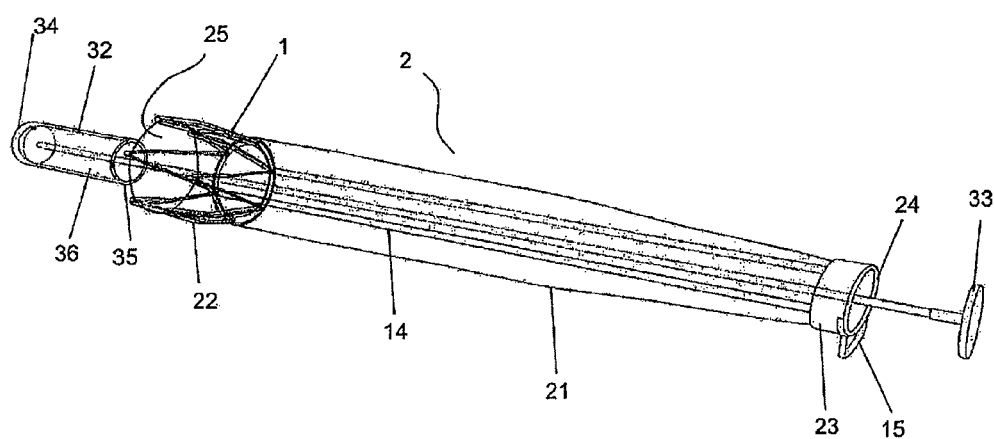
FIG. 6A shows the plunger of FIG. 6 housed within the internal axial conduit of the assembled internal component of FIG. 5C.
Figure 6B:
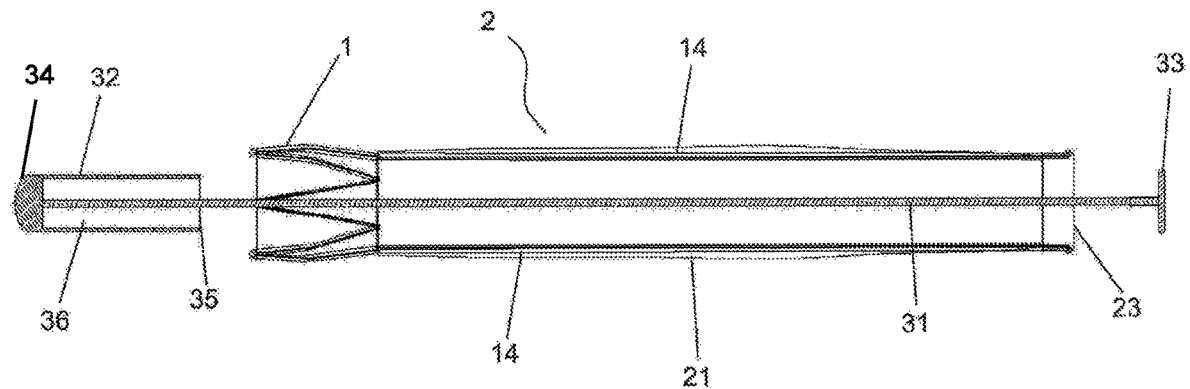
FIG. 6B shows a cross-section of the plunger of FIG. 6 housed within the internal axial conduit of the assembled internal component of FIG. 5C.

FIGS. 6A and 6B show plunger 3 housed within the internal axial conduit of assembled internal component 2. Head 32 of plunger 3 protrudes from opening 25 of assembled internal component 2. Base 33 protrudes from opening 24 of said assembled internal component 2. Insertion rod 31 is housed within or substantially within the axial conduit of said assembled internal component 2.

Owing to the pliant characteristics of collection component 1 and the material characteristics of transit component 21, collection component 1 and transit component 21 may be compressed by application of inwardly directed radial forces, and housed partially or wholly within cavity 36 in head 32. While insertion rod 31 of plunger 3 is housed within the axial conduit of assembled internal component 2, at least part of one or both of collection component 1 and transit component 21 may in turn be housed within head 32 of plunger 3.

FIG. 12 shows an insertion sleeve 7 that houses collection component 1 and transit component 21 either partially or completely during insertion. Insertion sleeve 7 comprises a hollow cylindrical or substantially cylindrical tube 71 open at both ends, having conduit 73 connecting said both ends. The internal radius of conduit 73 is selected to be larger than the radius of insertion rod 31.

The cross-sectional profile of insertion sleeve 7 may be small, and selected with a view to reduce trauma and foreign body sensation.

In an embodiment, tip 75 of one end of insertion sleeve 7 has a reduced cross-section in comparison to the cross-section of the rest of insertion sleeve 7, wherein tip 75 is dimensioned to provide an interference fit with the inner walls of cylindrical cavity 36 in head 32. The outer walls of insertion sleeve 7 may have a positive discontinuity 72, for providing abutment surfaces on the outer walls of the insertion device. Said positive discontinuity 72 may comprise loops, flanges, lips, or any other form of protuberance that would provide a suitable abutment surface. Positive discontinuity 72 provides a physical and visual indication of the depth to which insertion sleeve 7, and the insertion device has been deployed within the rectum, and in some cases may also act as a positive stop to prevent over-insertion by abutting against portions of the anatomy adjacent the anal opening (the patient's buttocks). Said positive discontinuity 72 also provides leverage to anchor the insertion device to the patient's buttocks, thereby facilitating one-handed operation of said insertion device.

In other embodiments of the insertion sleeve, the required physical or visual indication of depth or insertion by way of visible or radio-opaque marker bands or a color coding to assist a care provider in positioning collection component 1 within the rectum.

In the embodiment shown in FIG. 12, insertion sleeve 7 has a side slot 74, which permits for deploying therewithin and withdrawing therefrom, collection component 1 and transit component 21.

Figure 7:
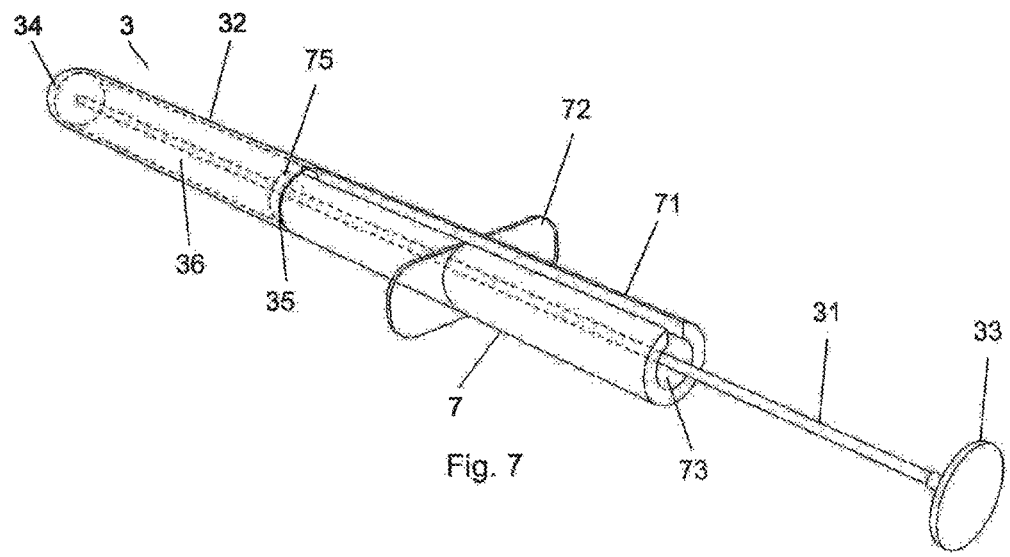
FIG. 7 shows the plunger of FIG. 6 having an insertion sleeve deployed thereon.

FIG. 7 shows plunger rod assembly 3 with insertion sleeve 7 deployed thereon, wherein insertion rod 31 passes through conduit 73. In the embodiment shown, tip 75 of insertion sleeve 7 provides the necessary interference fit with cavity 36 within head 32, thereby ensuring that insertion sleeve 7 does not disengage from head 32 without a positive application of force to disengage the two components.

Figure 8:
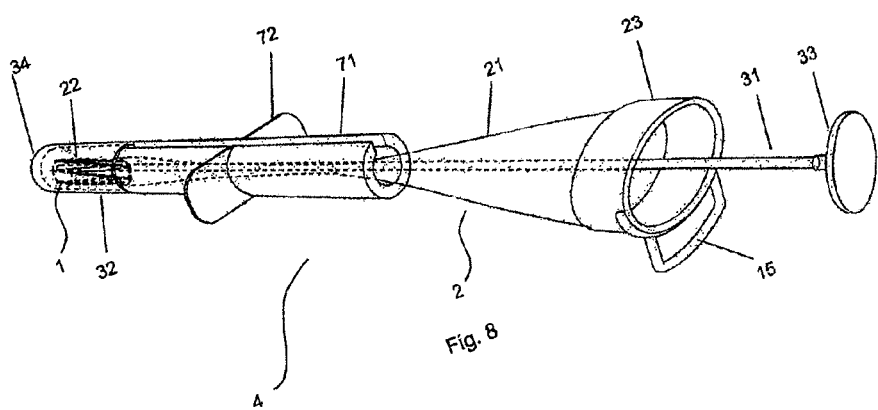
FIG. 8 shows the insertion device in a fully assembled state, wherein the collection component and at least a part of the transit component are housed within the plunger and insertion sleeve assembly of FIG. 7.

FIG. 8 shows insertion device 4 in a fully assembled state. Assembled internal component 2 houses insertion rod 31 of plunger 3 in the manner illustrated in FIG. 6A, and in turn at least part of one or both of collection component 1 and transit component 2 are housed within cavity 36 in head 32 of plunger 3.

In the embodiment shown in FIG. 8, at least part of one or both of collection component 1 and transit component 21 is housed within a conduit created by the plunger and insertion sleeve assembly of FIG. 7. Specifically, said conduit is a combined conduit comprising cavity 36 within head 32 and conduit 73 within insertion sleeve 7. In another embodiment, the conduit for housing said assembled internal component 2 comprises solely of conduit 73.

The pliant characteristics of collection component 1 permits for said component 1 to be compressed or collapsed and housed within the conduit provided by the at least one of the plunger and insertion sleeve assembly of FIG. 7. Similarly, characteristics of transit component 21 permit it to be compressed and housed within said conduit.

Both collection component 1 and transit component 21 are compressed or collapsed around insertion rod 31 housed therewithin. Said plunger rod 31 is accordingly also at least partially housed within the same conduit within which collection component 1 and transit component 21 are housed. Inner walls of the conduit provided by said at least one of the plunger and insertion sleeve assembly retain collection component 1 and transit component 21 in a collapsed state and prevent them from expanding.

It would be apparent to a person of skill in the art that internal diameter of conduit 73 within insertion sleeve 7 and of cavity 36 in head 32 of plunger 3 require to be chosen based on the respective dimensions of the components housed therewithin.

In the embodiment shown in FIG. 8, collection component 1 is housed within cavity 36 in head 32, and transit component 21 is partially housed within conduit 73 in insertion sleeve 7. The remainder of transit component 21 is permitted to trail outside insertion sleeve 7.

Figure 14:
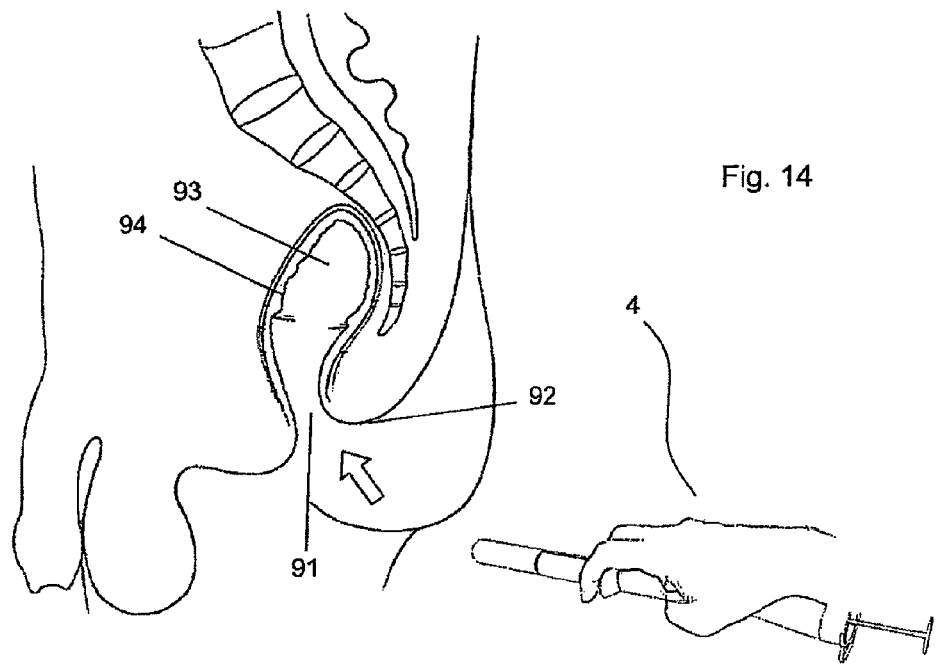
FIG. 14 shows the fully assembled insertion device of FIG. 8 ready for deployment in the rectum.
Figure 14A:
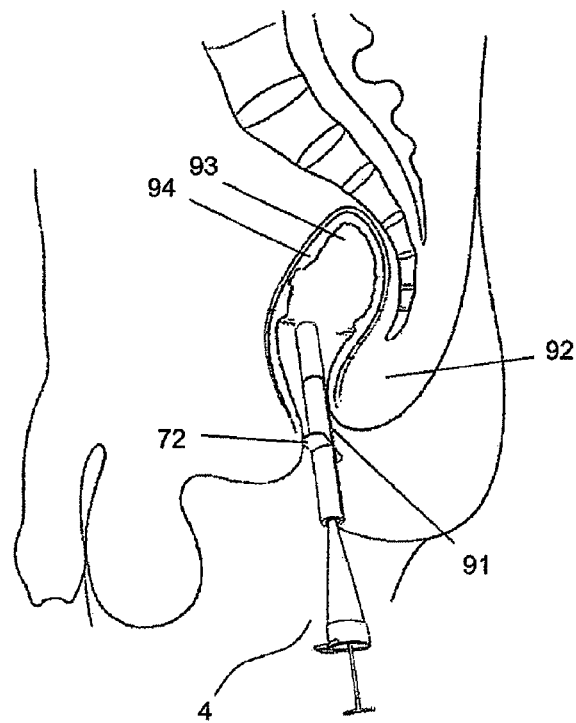
FIG. 14A shows the insertion device of FIG. 8 inserted into the rectum upto a predetermined depth or location.
Figure 14B:
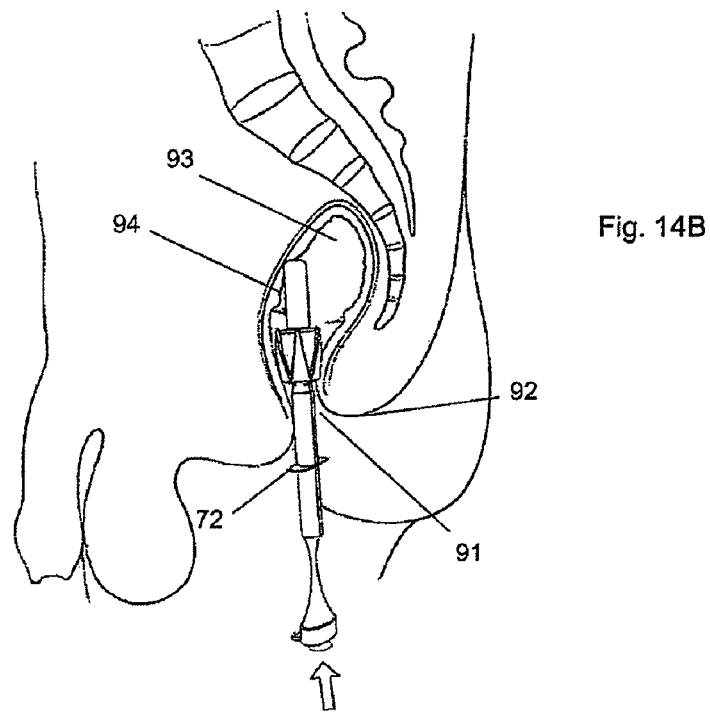
FIG. 14B shows deployment of the assembled internal component by application of an axially directed force on the plunger of FIG. 8 in a direction towards the collection component.
Figure 14C:
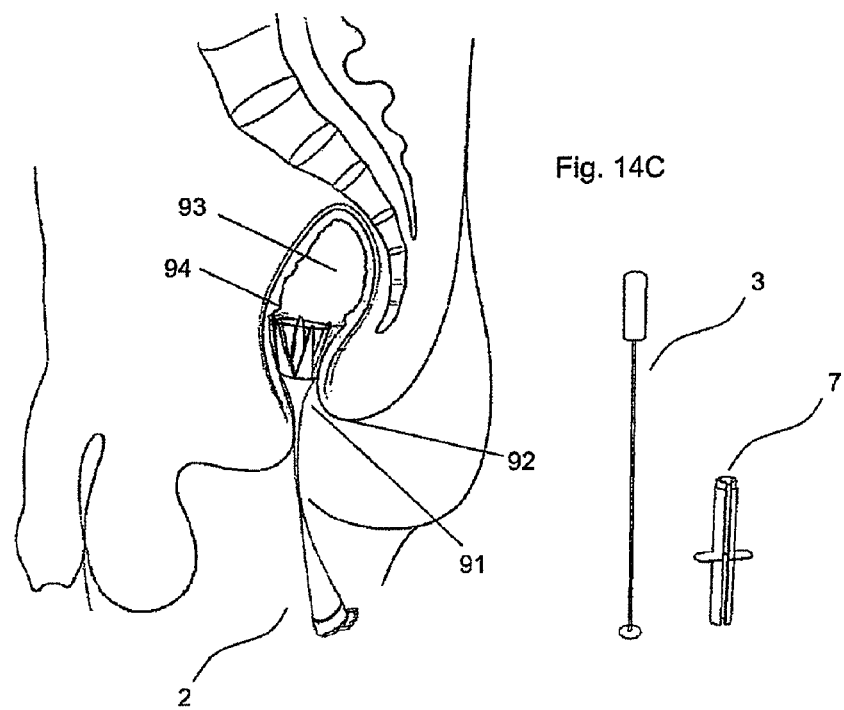
FIG. 14C shows the assembled internal component deployed in a desired location within the rectum, with the plunger and insertion sleeve of FIG. 8 having been withdrawn.

FIGS. 14 to 14C show the method of insertion and deployment of assembled internal component 2 within the rectum using insertion device 4 of FIG. 8.

In FIG. 14, a fully assembled insertion device 4 is ready for deployment. Facing the insertion device is a profile of the rectal anatomy, comprising an anal opening 91, adjacent anatomy comprising buttocks 92, the rectum 93 and rectal walls 94 for rectum 93.

FIG. 14A shows insertion device 4 inserted into the rectum, with capped end 34 entering anal opening 91 first. The device is inserted in rectum 93 to an appropriate depth determined by the care provider. In the preferred embodiment shown, the positive discontinuity 72 on insertion sleeve 7 provides an abutment surface that engages with adjacent anatomy 92, thereby preventing further insertion of the device.

It would be apparent to the skilled person that location of the positive discontinuity 72 on insertion sleeve 7 depends on the depth to which the insertion device 4 is desired to be deployed within rectum 93.

FIG. 14B illustrates deployment of assembled internal component 2 within rectum 93. Upon deployment of insertion device 4 to the desired depth within rectum 93, force directed upon base 33 of plunger 3 in the direction of collection component 1 causes insertion rod 31 to move in an axial direction relative to insertion sleeve 7, thereby causing head 32 to move in the same direction and simultaneously disengage from insertion sleeve 7. Assembled internal component 2 however remains in the same location relative to insertion sleeve 7, as a consequence of friction and interference between sheathing in assembled internal component 2 and the inner walls of conduit 73. Since assembled internal component 2 does not move, movement of plunger 3 causes displacement of head 32 relative to assembled internal component 2, including relative to collection component 1 housed within cavity 36 in head 32. Sufficient displacement of head 32 relative to collection component 1 causes said component 1 to exit cavity 36 entirely.

In absence of the barrier to expansion provided by the inner walls of cavity 36, collection component 1 expands and adheres to rectal walls 94 of rectum 93 in the desired manner. Insertion sleeve 7 may thereafter be removed by freeing such part of transit component 21 and insertion rod 31 as remain housed therewithin. In the embodiment shown in FIG. 7, the remainder of transit component 21 may be removed via side slot 74. Once insertion sleeve 7 is removed, plunger 3 may be withdrawn by applying force in the proximal direction, to base 33. The withdrawing force causes plunger 3 to be withdrawn through the internal axial conduit of assembled internal component 2, and may thus be removed entirely.

FIG. 14C shows collection component 1 and transit tube 21 deployed in a desired location within rectum 93, with the plunger 3 and insertion sleeve 7 of FIG. 8 having been withdrawn.

FIGS. 9, 10, 11, 13 and 13A show components for, and another embodiment of, a fully assembled device for insertion of assembled internal component 2 into the rectum.

Figure 9:
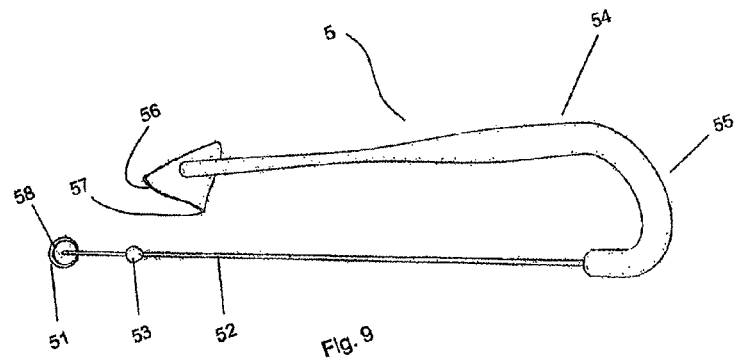
FIG. 9 shows an alternate embodiment of the plunger for the insertion device.

FIG. 9 shows a plunger 5 for the insertion device. Plunger 5 comprises a rigid or semi-rigid insertion rod 52 having a head 51, a looped base 55 and handle 54, which base 55 and handle 54 do not interfere with the anatomy, but provide significant assistance in safe insertion and deployment of assembled internal component 2 within the rectum. Head 51 may have a substantially spherical, cylindrical or conical tip, or a tip of any other shape that facilitates entry of plunger into rectum 93.

In a preferred embodiment, the leading portion of head 51 has a blunt rounded tip to facilitate insertion without trauma or discomfort. Looped base 55 and handle 54 provide a means for application of pressure to advance plunger 5, or for gripping to withdraw said plunger 5. In an embodiment, the trailing portion 58 of head 51 has a reduced cross-section in comparison to the cross-section of the remainder of head 51. As discussed below said reduced cross-section serves to provide an interference fit within conduit 84 of insertion sleeve 8.

Head 51 may be constructed from a variety of inert or biocompatible materials, including inter alia a soft, dermatissue friendly material. Further, said head 51 may be shaped so as to facilitate smooth, non-traumatic insertion and removal. Head 51 may have one or more coatings, a secondary substrate or substrates on its external surface, which improve lubricity while reducing tissue trauma and patient discomfort.

In a preferred embodiment, the cross-sectional profile of head 51 is small, and selected with a view to reduce trauma and foreign body sensation.

Handle 54 provides an abutment surface 56 for abutment against portions of anatomy 92 adjacent to the anal opening 91. Said abutment surface 56 may without limitation comprise shelves, flanges, lips, or any other barrier structure or protuberance that would provide an adequate abutment surface. Abutment surface 56 provides a physical and visual indication of the depth to which the insertion device has been deployed within rectum 93, and in some cases acts as a positive stop to prevent over-insertion by abutting against portions of the anatomy 92 adjacent to the anal opening 91. In particular embodiments of plunger 5, the required physical or visual indication of depth or insertion may be provided by visible or radio-opaque marker bands or a color coding.

Abutment surface 56 also provides a locking mechanism 57, the objective and construction whereof are discussed below.

In an embodiment, insertion rod 52 has a positive discontinuity 53 located between looped base 55 and head 51. Positive discontinuity 53 provides an abutment surface on the insertion rod 52. Said positive discontinuity 53 may comprise beads, loops, flanges, lips, or any other protuberance that would provide an adequate abutment surface. The cross-sectional profile of positive discontinuity 53 is selected so as to permit free movement of insertion rod 52 within insertion sleeve 8.

As with the embodiment shown in FIG. 6A, during assembly of the insertion device, insertion rod 52 of plunger 5 is housed within the internal axial conduit of assembled internal component 2. Head 51 of plunger 5 protrudes from opening 25 of assembled internal component 2. Base 55 protrudes from opening 24 of said assembled internal component 2. Insertion rod 52 is housed within or substantially within the axial conduit of said assembled internal component 2.

FIGS. 13 and 13A show an insertion sleeve 8, for housing the assembled internal component 2 either partially or completely during insertion. Insertion sleeve 8 comprises a hollow cylindrical or substantially cylindrical tube 71 open at both ends, having conduit 84 connecting said both ends. The internal radius of conduit 73 is dimensioned to be larger than the radius of insertion rod 52 for corresponding plunger 5.

At least one end of insertion sleeve 8 is provided with opposed flanges or handles 82 for manipulation of said insertion sleeve 8.

The inner diameter of conduit 84 is chosen to correspond to the cross-section of trailing portion 58 of head 51, such that trailing portion 58 provides an interference fit with the inner walls of conduit 84, thereby providing for engagement between head 51 and insertion sleeve 8.

In a preferred embodiment, the cross-sectional profile of insertion sleeve 8 is small, and selected with a view to reduce trauma and foreign body sensation.

In the embodiment shown in FIG. 13, insertion sleeve 8 has at least one weakened wall portion 83. Said wall portion 83 is weakened in an axial direction from one end of insertion sleeve 8 to the other. Application of simultaneous outwardly directed radial force to opposed flanges or handles 82 causes for insertion sleeve 8 to tear along weakened wall portion 83, thereby creating a side slot for removal of any component housed within. In the embodiment shown in FIG. 13A, insertion sleeve 8 has at least two weakened wall portions 83 on opposite sides of the sleeve circumference. Application of opposing forces on flanges or handles 82 cause insertion sleeve 8 to tear along both weakened wall portions 83, thereby separating into two segments 81A and 81B and facilitating removal of said insertion sleeve 8 from around any component housed within.

Wall portions of insertion sleeve 8 may be weakened in a variety of ways that would be apparent to a skilled person in view of the particular materials of construction for an insertion sleeve, including inter alia using perforations, weak constructional material, pre-stressing of material, and prior separation of the insertion sleeve along the desired weakened wall portion and subsequent reattachment using an appropriate adhesive. In another embodiment, frangible insertion sleeve 8 may be assembled and attached using inter alia one or more of adhesives, a snap-fit mechanism, shrink tubes or mechanical clips, staples, pins, removable bands.

The insertion sleeve may be made of a variety of materials including metals, alloys, thermoplastic polymers, natural or synthetic elastic or compliant materials. The insertion sleeve may be coated or uncoated, both internally and externally. Coatings may be selected from the group of hydrophilic, hydrophobic, friction enhancing, friction reducing, antimicrobial, anesthetic and anti-inflammatory coatings. The outside and inside surfaces of the insertion sleeve may have the same or different coatings, single or multiple coatings, and on single or multiple locations to enhance desired behavior and properties.

Figure 10:
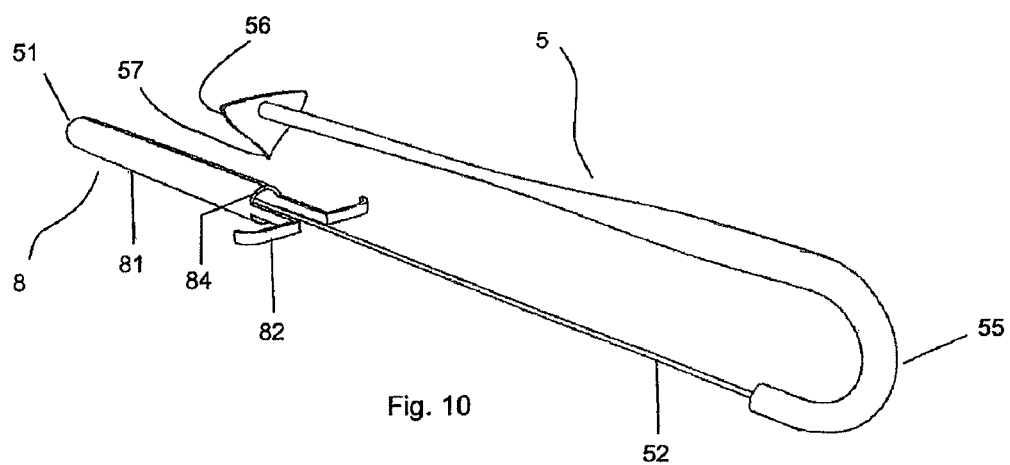
FIG. 10 shows the plunger of FIG. 9 having an alternate embodiment of the insertion sleeve deployed thereon.

FIG. 10 shows plunger 5 with insertion sleeve 8 deployed thereon, wherein insertion rod 52 passes through conduit 84. In the embodiment shown, trailing portion 58 of head 51 provides an interference fit with the inner walls of conduit 84, thereby providing an interference fit and ensuring that insertion sleeve 8 does not disengage from head 51 without a positive application of force for disengagement. The embodiment in FIG. 10 also demonstrates the locking mechanism provided on plunger 5. Abutment surface 56 provides a lock 57 comprising any one of a flange, notch, lip, interference link, clutch, ratchet, or wrap and sealed components. Said lock 57 engages with the proximal end of insertion sleeve 8, and prevents axial movement of insertion sleeve 8 relative to insertion rod 52 in a proximal direction. Lock 57 ensures that insertion sleeve 8 is not axially displaced in a proximal direction during insertion in the rectum 93, as a result of resistance at the anal opening 91 or from rectal walls 94 of rectum 93.

When insertion sleeve 8 is required to be withdrawn in a proximal direction, lock 57 is first disengaged by moving it away from the lip of insertion sleeve 8. Construction of looped base 55 and handle 54 is such as to confer sufficient flexibility to enable such movement. Insertion sleeve 8 may thereafter be withdrawn in a proximal direction.

Figure 11:
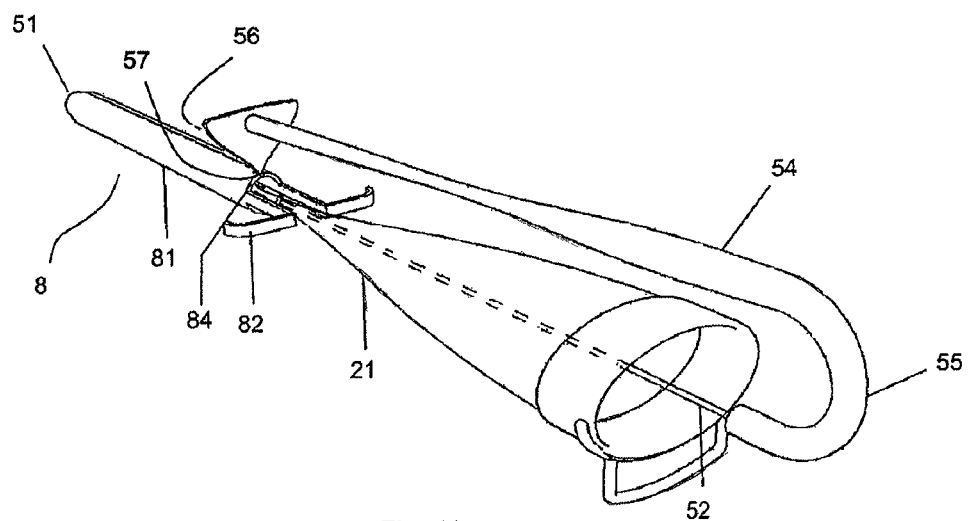
FIG. 11 shows an alternate embodiment of the insertion device in a fully assembled state, wherein the collection component and at least a part of the transit component are housed within the plunger and insertion sleeve assembly of FIG. 10.

FIG. 11 shows insertion device 4 in a fully assembled state. Assembled internal component 2 houses insertion rod 52 of plunger 5 in the manner discussed above.

In the embodiment shown in FIG. 11, collection component 1 and at least part of transit. Component 2 are housed within conduit 84 in insertion sleeve 8.

The pliant characteristics of collection component 1 permits for said component 1 to be compressed or collapsed and housed within conduit 84. Similarly, the characteristics of transit component 21 permit for it to be compressed and housed at least partially within said conduit 84. It would be noted that both collection component 1 and transit component 21 are compressed or collapsed around insertion rod 52 housed therewithin. Said plunger rod 52 is accordingly also housed at least partially within conduit 84. Collection component 1 is collapsed around plunger rod 52 in a manner such that proximal end 17 engages with the abutment surface provided by positive discontinuity 53 on insertion rod 52.

The internal diameter of conduit 84 in insertion sleeve 8 may be selected based on the respective dimensions of the components intended for housing therewithin.

Figure 15:
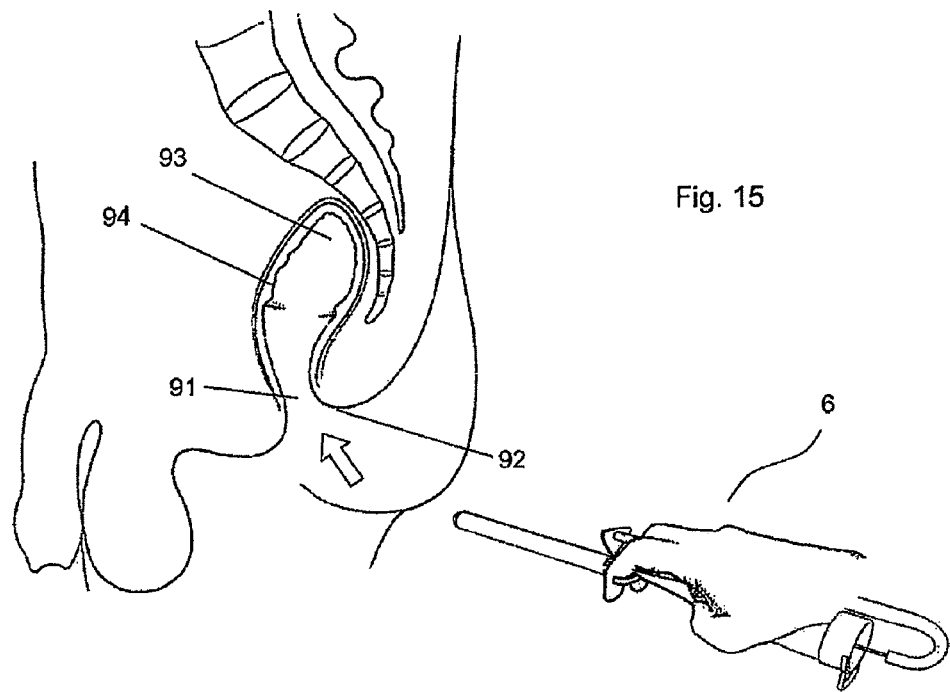
FIG. 15 shows the fully assembled insertion device of FIG. 11 ready for deployment in the rectum.
Figure 15A:
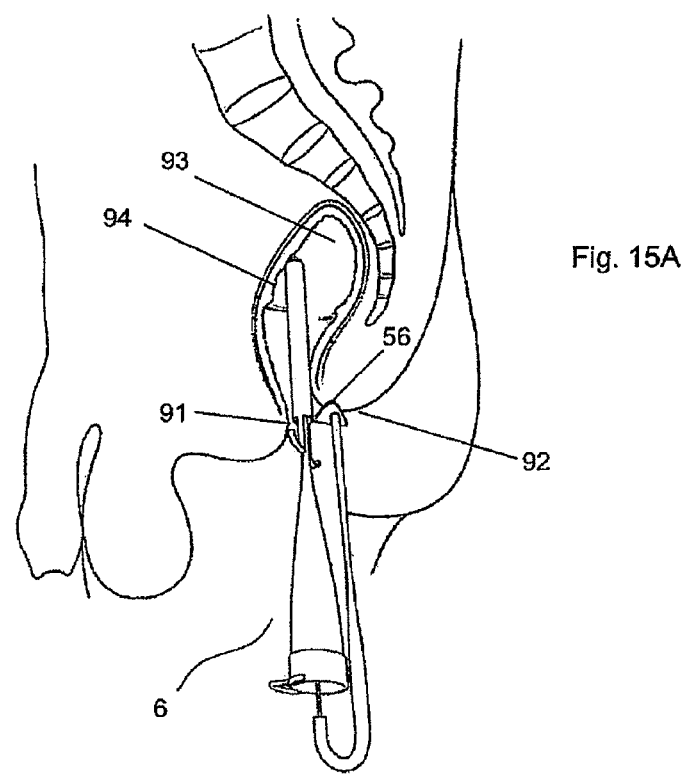
FIG. 15A shows the insertion device of FIG. 11 inserted into the rectum upto a predetermined depth or location.
Figure 15B:
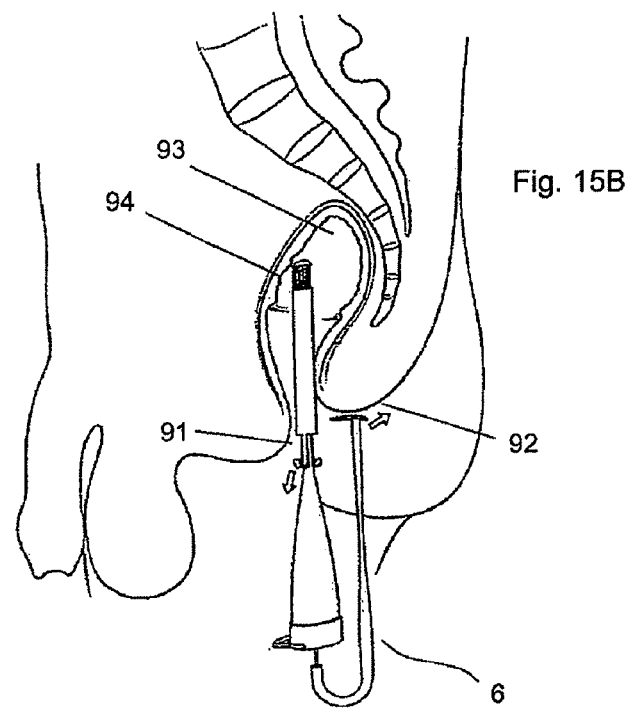
FIG. 15B shows the insertion device of FIG. 11 after insertion into the rectum, wherein a locking mechanism is disengaged, and withdrawal of the insertion sleeve is commenced.
Figure 15C:
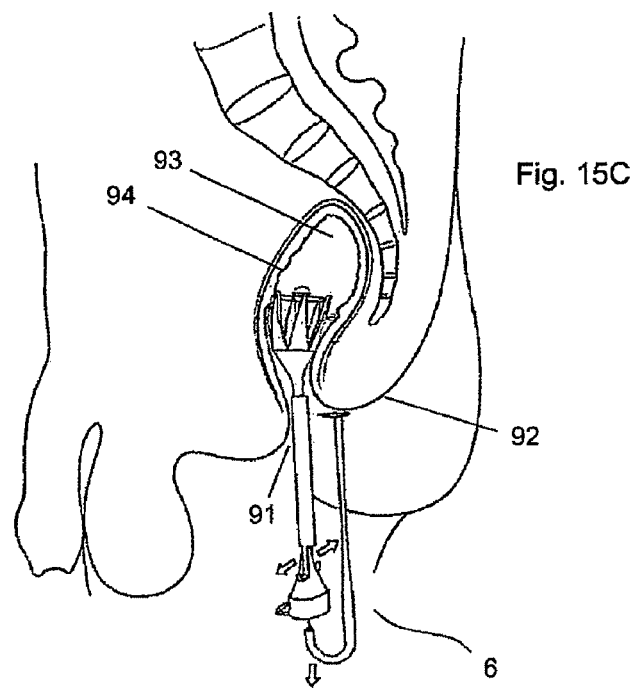
FIG. 15C shows the deployment of the collection component by withdrawal of the insertion sleeve of FIG. 11, in a direction away from the collection component.
Figure 15D:
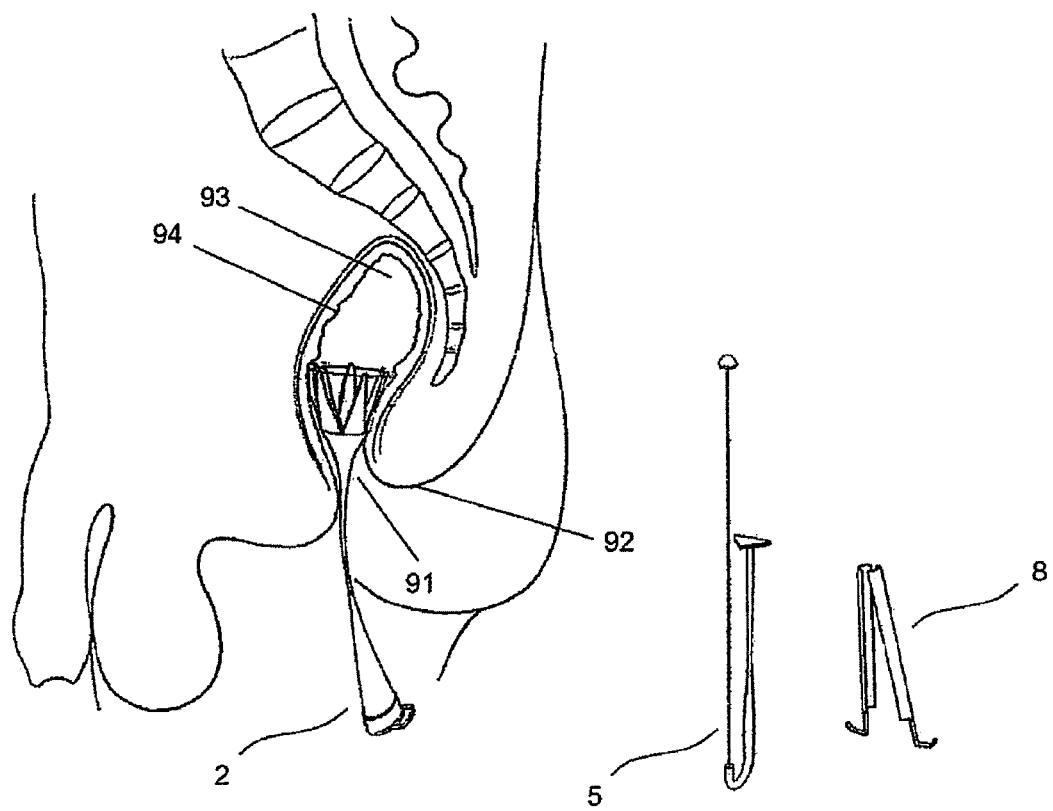
FIG. 15D shows the collection component and transit tube deployed in a desired location within the rectum, with the plunger and insertion sleeve of FIG. 11 having been withdrawn.
Figure 16:
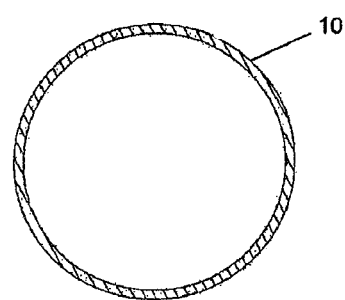
FIG. 16 shows a plan view cross-section of a retaining member of a prior art indwelling catheter in its fully expanded state.
Figure 16A:
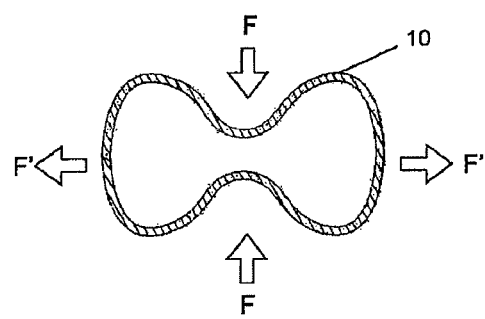
FIG. 16A shows a plan view cross-section of a retaining member of a prior art indwelling catheter when inwardly directed radial forces are applied at specific points on its circumference.
Figure 17:
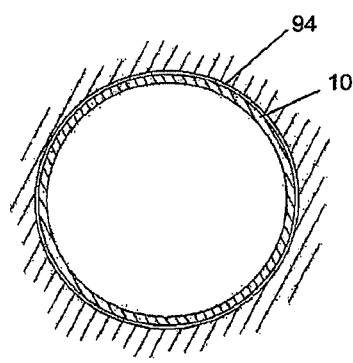
FIG. 17 shows a plan view cross-section of a retaining member of a prior art indwelling catheter in its fully expanded state when disposed within the rectum.
Figure 17A:
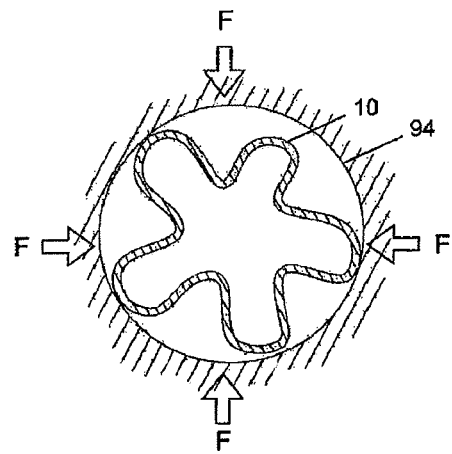
FIG. 17A shows a plan view cross-section of a retaining member of the prior art indwelling catheter when disposed within the rectum while the rectum undergoes a peristaltic contraction.

FIGS. 15 to 15D show the method of insertion and deployment of assembled internal component 2 within rectum 93 using insertion device 6 of FIG. 11.

In FIG. 15, fully assembled insertion device 6 is ready for deployment. Facing insertion device 6 is a profile of the rectal anatomy, comprising anal opening 91, adjacent anatomy comprising buttocks 92, rectum 93 and rectal walls 94 of rectum 93.

FIG. 15A shows insertion device 6 inserted into rectum 93, with head 51 entering anal opening 91 first. The insertion device 6 is inserted in rectum 93 to an appropriate depth determined by the care provider. In the embodiment shown, abutment surface 56 on plunger 5 engages with adjacent anatomy 92, thereby, preventing further insertion of the device 6.

It would be apparent to the skilled person that location of abutment surface 56 on handle 54 depends on the depth to which insertion device 6 is desired to be deployed within rectum 93.

FIG. 15B illustrates deployment of assembled internal component 2 within rectum 93. Upon deployment of insertion device 6 to the desired depth within rectum 93, lock 57 is disengaged and insertion sleeve 8 is withdrawn in an axially proximal direction, relative to plunger 5 and its components. Since plunger 5 remains stationary, withdrawal of insertion sleeve 8 causes said sleeve 8 to disengage from head 51. Assembled internal component 2 is prevented from simultaneously moving in the proximal direction by engagement between proximal end 17 and positive discontinuity 53 on insertion rod 52.

As shown in FIG. 15C, neither assembled internal component 2 nor plunger 5 is permitted to move in a proximal direction. Movement of insertion sleeve 8 in the proximal direction accordingly displaces collection component 1 relative to said sleeve 8. Sufficient displacement of insertion sleeve 8 relative to collection component 1 causes said component 1 to exit said sleeve 8 entirely.

In absence of the barrier to expansion earlier provided by the inner walls of conduit 84 in insertion sleeve 8, collection component 1 expands and adheres to rectal walls 94 of rectum 93 in the desired manner. Insertion sleeve 8 may then be removed entirely from rectum 93 and thereafter from around assembled internal component 2 by fracturing or tearing along its weakened wall portions and removing it entirely. Once insertion sleeve 8 is removed, plunger 5 may be withdrawn by applying a force in the proximal direction to handle 54 or looped base 55. The withdrawing force causes plunger 5 to be withdrawn through the internal axial conduit of assembled internal component 2, and thus removed entirely.

FIG. 15D shows collection component 1 and transit tube 21 deployed in a desired location within rectum 93, with plunger 5 and insertion sleeve 8 of FIG. 11 having been completely withdrawn.

In other embodiments of the invention, the withdrawal mechanism may be mechanically, hydraulically or pneumatically activated and assisted. The withdrawal mechanism may be self-activated based on internal or external triggers such as time based triggers or material properties (e.g. biodegradable polymers). The withdrawal mechanism may also have in-built secondary components, where such components aide the user in, visually or intuitively, determining length of the withdrawal stroke, securing the insertion device at its optimal location within the rectum, or determining the position from which the insertion device may be optimally withdrawn from rectum 93.

In a particular embodiment, the insertion assemblies 4 and 6 are designed for single use and may be constructed from eco-friendly and biodegradable material.

What is claimed is:

1. A device for collecting material from a rectum, the device comprising:
   an annular collection component forming a lumen extending between an open proximal end and a distal end in a longitudinal axis, the collection component comprising a plurality of annular elements, each annular element extending around the lumen along the longitudinal axis and having arms arranged in a sinusoidal or zig-zag pattern forming a series of peaks and troughs, the sinusoidal or zig-zag pattern extending radially around the longitudinal axis, wherein the collection component is expandable from a compressed configuration to an expanded configuration, further wherein the plurality of annular elements impel the collection component from the compressed configuration toward the expanded configuration, and wherein the plurality of annular elements are configured to exert outwardly directed radial pressure of between 1 to 106 cm of water against the rectum walls upon deployment within the rectum, so that the peaks and troughs of the plurality of annular elements abut the rectum walls and anchor the plurality of annular elements against the rectum walls to retain the device within the rectum;
   a conduit for material to migrate from the collection component, the conduit comprising a flexible, tubular sheath having a first open end, a second end, and a lumen, wherein the first open end is in connection with the open proximal end of the collection component; and
   a filament coupled to the collection component and configured to collapse the collection component and reduce the outer and inner diameters of the collection component when pulled proximally, wherein the filament extends proximally beyond the collection component.

2. The device according to claim 1, wherein the collection component is overlaid with a flexible and resilient material.

3. The device according to claim 1, wherein the first annular element comprises a plurality of adjacent arms connected in the sinusoidal or zig-zag pattern around the lumen.

4. The device according to claim 1, wherein the arms of the first annular element comprises a continuous strand of resilient wire material arranged in the sinusoidal or zig-zag pattern around the lumen.

5. The device of claim 1, wherein the first and second annular elements are configured to exert outwardly directed radial pressure of between 1 to 48 cm of water against the rectum walls upon deployment within the rectum.

6. The device of claim 1, further wherein the first and second annular elements are configured to exert outwardly directed radial pressure of between 10 to 30 cm of water against the rectum walls upon deployment within the rectum.

7. The device of claim 1, wherein an external diameter of the first and second annular elements are configured to contact the rectum.

8. The device of claim 1, wherein an external diameter of the first and second annular elements in the expanded configuration is between 20 mm and 60 mm.

9. The device of claim 1, wherein an external diameter of the first and second annular elements in the compressed configuration is between 6 mm and 21 mm.

10. The device of claim 1, wherein an device includes at least two filaments coupled to a handle for pulling the at least two filaments proximally.

11. A device for collecting material from a rectum, the device comprising:
- an annular collection component forming a lumen extending between an open proximal end and a distal end in a longitudinal axis, the collection component comprising an annular element having arms arranged in a sinusoidal or zig-zag pattern forming a series of peaks and troughs, the sinusoidal or zig-zag pattern extending radially around the longitudinal axis, the annular element extending around the lumen, wherein the collection component is expandable from a compressed configuration to an expanded configuration, further wherein the annular element impels the collection component from the compressed configuration toward the expanded configuration, and wherein the annular element is configured to exert outwardly directed radial pressure of between 1 to 106 cm of water against the rectum walls upon deployment within the rectum, so that the peaks and troughs of the annular element abut the rectum walls and anchor the annular element against the rectum walls; and
- a conduit for material to migrate from the collection component, the conduit comprising a flexible, tubular sheath having a first open end, a second end, and a lumen, wherein the first open end is in connection with the open proximal end of the collection component; and
- a filament coupled to the collection component and configured to collapse the annular elements when pulled proximally, wherein the filament extends proximally beyond the collection component.

12. The device according to claim 11, wherein at least one of an inner or outer contour of the collection component is overlaid with a flexible and resilient material.

13. The device according to claim 11, further comprising a receptacle coupled to a second end of the conduit.

14. The device according to claim 11, wherein a wall portion connecting the open proximal end and the distal end of the collection component is at an outwardly directed angle of between 10° and 30° relative to a central axis through the lumen of the collection component.

15. The device according to claim 11, wherein the annular element comprise a single continuous strand of resilient wire material arranged in the sinusoidal or zig-zag pattern.

16. The device according to claim 11, wherein the annular element is a first annular element, wherein the collection component comprises a second annular element longitudinally offset from the first annular element and arranged in a sinusoidal or zig-zag pattern forming a series of peaks and troughs circumferentially around the longitudinal axis through the lumen.

17. The device according to claim 11, wherein the length of the collection component is between 10 mm and 50 mm.

18. The device according to claim 11, further wherein the annular element is configured to exert outwardly directed radial pressure of between 1 to 48 cm of water against the rectum walls upon deployment within the rectum.

19. The device according to claim 11, further wherein the annular element is configured to exert outwardly directed radial pressure of between 10 to 30 cm of water against the rectum walls upon deployment within the rectum.

20. The device of claim 11, wherein an external diameter of the annular element is configured to contact the rectum walls.

21. The device of claim 11, wherein an external diameter of the annular element in the expanded configuration is between 20 mm and 60 mm.

22. The device of claim 11, wherein an external diameter of the annular element in the compressed configuration is between 6 mm and 21 mm.

* * * * *